(12) United States Patent
Pedersen et al.

US009271494B2

(10) Patent No.: US 9,271,494 B2
(45) Date of Patent: Mar. 1, 2016

(54) SHELF STABLE, REDUCED CORROSION, READY TO USE PEROXYCARBOXYLIC ACID ANTIMICROBIAL COMPOSITIONS

(75) Inventors: Daniel E. Pedersen, Cottage Grove, MN (US); Katherine Joan Molinaro, Inver Grove Heights, MN (US); Michael Besse, Golden Valley, MN (US)

(73) Assignee: Ecolab USA, Inc., St. Paul, MN (US)

( * ) Notice: Subject to any disclaimer, the term of this patent is extended or adjusted under 35 U.S.C. 154(b) by 1274 days.

(21) Appl. No.: 11/847,604

(22) Filed: Aug. 30, 2007

(65) Prior Publication Data

US 2009/0061017 A1    Mar. 5, 2009

(51) Int. Cl.
*A01N 59/00* (2006.01)
*A01N 37/16* (2006.01)
*A61L 2/18* (2006.01)

(52) U.S. Cl.
CPC ............. *A01N 37/16* (2013.01); *A61L 2/186* (2013.01); *A61L 2202/24* (2013.01)

(58) Field of Classification Search
CPC ............................. A01N 37/16; A61L 2/186
See application file for complete search history.

(56) References Cited

U.S. PATENT DOCUMENTS

| | | | |
|---|---|---|---|
| 2,590,856 A * | 4/1952 | Greenspan et al. | 514/557 |
| 4,297,298 A * | 10/1981 | Crommelynck et al. | 562/3 |
| 4,404,040 A * | 9/1983 | Wang | 134/22.14 |
| 4,647,392 A | 3/1987 | Darden et al. | |
| 4,743,447 A | 5/1988 | Le Rouzic et al. | |
| 5,200,189 A | 4/1993 | Oakes et al. | |
| 5,314,687 A | 5/1994 | Oakes et al. | |
| 5,409,713 A | 4/1995 | Lokkesmoe et al. | |
| 5,437,868 A | 8/1995 | Oakes et al. | |
| 5,489,434 A | 2/1996 | Oakes et al. | |
| 5,565,231 A * | 10/1996 | Malone et al. | 426/532 |
| 5,616,335 A * | 4/1997 | Nicolle et al. | 424/405 |
| 5,718,910 A | 2/1998 | Oakes et al. | |
| 5,733,474 A * | 3/1998 | Kagermeier et al. | 252/186.25 |
| 5,900,256 A | 5/1999 | Scoville, Jr. et al. | |
| 6,010,729 A | 1/2000 | Gutzmann et al. | |
| 6,111,963 A | 8/2000 | Thompson, III | |
| 6,277,414 B1 * | 8/2001 | Elhaik et al. | 424/616 |
| 6,444,230 B1 | 9/2002 | Godin et al. | |
| 6,514,556 B2 | 2/2003 | Hilgren et al. | |

(Continued)

FOREIGN PATENT DOCUMENTS

EP      1252819      10/2002
WO   WO 8808667 A1 *  11/1988

OTHER PUBLICATIONS

Rosenberg et al.; "Schaum's Outline Series: College Chemistry" 2000, McGraw Hill Inc., (p. 108),pp. 1-3.*
Kitis, Mehmet; "Disinfection of wastewater with peracetic acid: a review," 2003, Elsiver, Environment International, vol. 30, pp. 47-55.*

(Continued)

*Primary Examiner* — Suzanne Ziska
*Assistant Examiner* — Ivan Greene
(74) *Attorney, Agent, or Firm* — McKee, Voorhees & Sease, PLC

(57) ABSTRACT

The present invention relates to shelf stable and/or less corrosive peroxycarboxylic acid antimicrobial compositions, including ready-to-use compositions. Shelf stable compositions can include defined ratios of hydrogen peroxide to peroxycarboxylic acid and/or hydrogen peroxide to protonated carboxylic acid, but need not include strong acid. Reduced corrosion compositions can include carboxylic acid and corrosion inhibitor at acid pH. Compositions of the invention can have advantageous activity against spores.

21 Claims, 1 Drawing Sheet

(56) References Cited

U.S. PATENT DOCUMENTS

| | | |
|---|---|---|
| 6,627,657 B1 | 9/2003 | Hilgren et al. |
| 6,674,538 B2 | 1/2004 | Takahashi |
| 6,927,237 B2 * | 8/2005 | Hei et al. .................. 514/557 |
| 2007/0158612 A1 | 7/2007 | Maes et al. |
| 2007/0219270 A1 * | 9/2007 | Bruggeman .................. 514/558 |

OTHER PUBLICATIONS

SEPIC SA—EP 1252819A1—English Abstract, 1 page, published Oct. 30, 2002.

European Patent Office, "Supplementary European Search Report" issued in connection to International Application No. PCT/IB2008/052265, 8 pages, mailed Feb. 4, 2015.

* cited by examiner

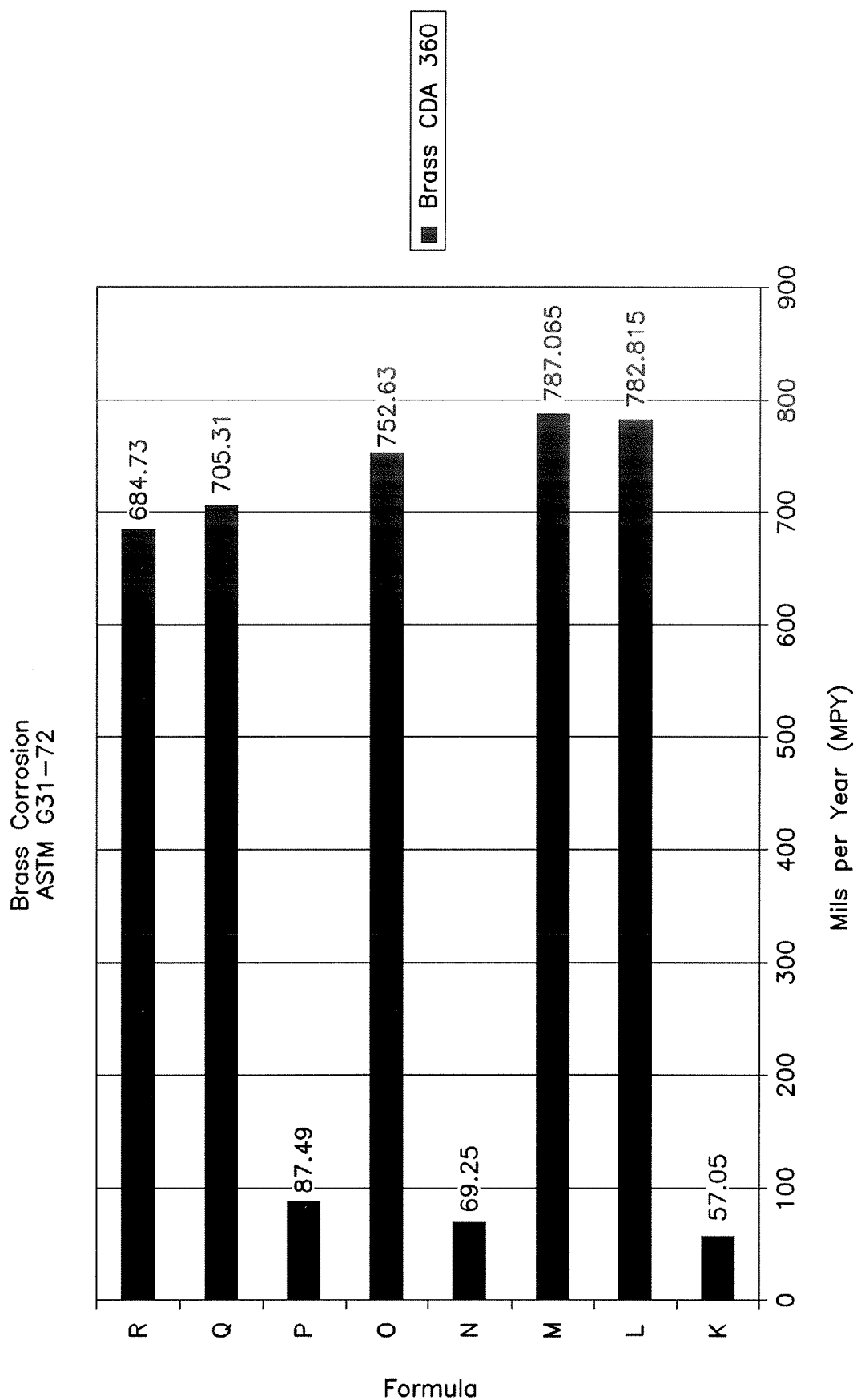

SHELF STABLE, REDUCED CORROSION, READY TO USE PEROXYCARBOXYLIC ACID ANTIMICROBIAL COMPOSITIONS

FIELD OF THE INVENTION

The present invention relates to shelf stable and/or less corrosive peroxycarboxylic acid antimicrobial compositions, including ready-to-use compositions. Shelf stable compositions can include defined ratios of hydrogen peroxide to peroxycarboxylic acid and/or hydrogen peroxide to protonated carboxylic acid, but need not include strong acid. Reduced corrosion compositions can include carboxylic acid and corrosion inhibitor at acid pH. Compositions of the invention can have advantageous activity against spores.

BACKGROUND OF THE INVENTION

Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556). Conventional peroxycarboxylic compositions including components such as hydrogen peroxide or mineral acid can be corrosive and, at use dilutions, may not have a sufficiently long shelf life. In addition, some conventional peroxycarboxylic acid compositions could benefit from increased sporicidal activity.

At neutral and basic pH, corrosion of soft and hard metal surfaces can be inhibited by mixtures of salts of aliphatic carboxylic acids and triazole compounds. Such mixtures are used, for example, in engine antifreeze compositions (see, e.g., U.S. Pat. No. 4,647,392). At basic pH, it is believed that the positively charged ion in the salt of the carboxylic acid is attracted to the electronegative surface of the target metal. The aliphatic portion of the carboxylic acid is believed to keep water away from the metal and thus provide a protective coating against corrosion. Such a mechanism cannot explain corrosion protection at acid pH and these compositions have not previously been shown effective at low pH.

Ongoing research efforts have strived for improved peroxycarboxylic acid compositions. In particular, these efforts have strived for compositions that have increased activity as a sporicide, that have a prolonged shelf life at use dilutions, and/or have reduced corrosiveness.

SUMMARY OF THE INVENTION

The present invention relates to shelf stable and/or less corrosive peroxycarboxylic acid antimicrobial compositions, including ready-to-use compositions, which can have advantageous sporicidal activity.

In an embodiment, shelf stable compositions include defined ratios of hydrogen peroxide to peroxycarboxylic acid and/or hydrogen peroxide to protonated carboxylic acid, but do not include substantial strong acid. In an embodiment the shelf stable composition includes peroxycarboxylic acid, hydrogen peroxide, and carboxylic acid, but lacks any significant catalytic or stabilizing concentration of strong acid. The composition can include hydrogen peroxide and peroxycarboxylic acid in a ratio of about 30:1 to about 60:1. The composition can include hydrogen peroxide and protonated carboxylic acid in a ratio of about 1:1 to about 2:1. The composition can be sufficiently stable that greater than 85% of the initial concentration of peroxycarboxylic acid remains after 1 year of storage at room temperature.

In an embodiment, reduced corrosion compositions include carboxylic acid and corrosion inhibitor at acid pH. In an embodiment the shelf stable composition includes peroxycarboxylic acid, hydrogen peroxide, medium chain mono carboxylic acid or benzoic acid derivative (e.g., benzoic acid or salicylic acid), corrosion inhibitor, and buffer at acid pH. Suitable pH includes about 1 to about 4. In an embodiment, the composition corrodes brass at a rate of less than about 250 mil per year.

The compositions can include short chain peroxycarboxylic acid, medium chain peroxycarboxylic acid, or a mixture thereof. The compositions can also include sequestrant, hydrotrope, surfactant, or combination thereof.

BRIEF DESCRIPTION OF THE FIGURES

FIG. 1 is a graph showing low corrosion by compositions according to the present invention and including a medium chain carboxylic acid and a corrosion inhibitor at acid pH.

DETAILED DESCRIPTION OF THE INVENTION

Definitions

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods any mineral acid; unless such a mineral acid is specifically listed after the phrase.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or that is generated in a minor side reaction during formation or degradation of the peroxycarboxylic acid.

As used herein, the term "strong acid" refers to an acid such a mineral acid such as sulfuric acid, phosphoric acid, nitric acid, and hydrochloric acid; or a strong organic acid such as methane sulfonic acid, ethane sulfonic acid, propane sulfonic acid, butane sulfonic acid, xylene sulfonic acid, and benzene sulfonic acid. Mineral and other strong acids are conventional catalysts for conversion of carboxylic acid to peroxycarboxylic acid. Unsubstituted alkyl carboxylic acids (e.g., short chain and medium chain carboxylic acids) and benzoic acid derivatives (e.g., benzoic acid and salicylic acid) are not strong acids.

As used herein, the term "corrosion" refers to noticeable dissolution of the metal, e.g., soft metal, from surfaces or articles which disfigures, modifies or otherwise causes interference with the intended functionality or appearance of the metal.

As used herein, the terms "mixed" or "mixture" when used relating to "peroxycarboxylic acid composition", "peroxycarboxylic acids", "percarboxylic acids", or "carboxylic acids" refer to a composition or mixture including more than one peroxycarboxylic acid or carboxylic acid, such as a composition or mixture including peroxyacetic acid and peroxyoctanoic acid or acetic acid and octanoic acid.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors. Objects also include the body or part of the body of a living creature, e.g., a hand.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, egg products, ready to eat food, grain (e.g., wheat), seeds, roots, tubers, leafs, stems, corms, flowers, nuts, sprouts, seasonings, or a combination or mixture thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like. Waters also include poultry feed waters and waters in dental water lines.

As used herein, the phrase "health care surface" refers to a surface of an instrument, a device, a cart, a cage, furniture, a structure, a building, facility, or surface therein, or the like that is employed as part of a health care activity. Health care surfaces include surfaces or equipment in or of an ambulatory care suite or in or of a long term care environment. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care. Health care surfaces include dental water lines.

As used herein, the term "instrument" refers to the various medical or dental instruments or devices that can benefit from cleaning with a stabilized composition according to the present invention.

As used herein, the phrases "medical instrument", "dental instrument", "dentistry instrument", "medical device", "dental device", "medical equipment", or "dental equipment"

refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, "residential" or "institutional" objects or surfaces include those found in structures inhabited by humans and encountered in general housekeeping. Such objects or surfaces include bathroom surfaces (e.g., fixture, floor and wall); lavatory surfaces (e.g., fixture, floor and wall), drains, drain surfaces, kitchen surfaces, and the like.

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

For the purpose of this patent application, successful microbial reduction is achieved when the microbial populations are reduced by at least about 90%, or by significantly more than is achieved by a flush with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used herein, the term "sterilant" refers to an agent that destroys all viable forms of microbial life.

As used in this invention, the term "sporicide" refers to a physical or chemical agent or process having the ability to cause greater than a 90% reduction (1-log order reduction) in the population of spores of *Bacillus subtilis, Clostridium difficile*, or *Clostridium sporogenes* within 30 min at room temperature. In certain embodiments, the sporicidal compositions of the invention provide greater than a 99% reduction (2-log order reduction), greater than a 99.99% reduction (4-log order reduction), greater than a 99.999% reduction (5-log order reduction) in such population, or total inactivation of endospores within 30 min at room temperature. In an embodiment, the present sporicidal composition eliminates all bacterial endospores within the stated time and temperature, e.g., 30 min at room temperature. Such a test can start with at least $10^4$ spores on each carrier suture.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, biostatic. A sanitizer and a disinfectant are, by definition, agents which provide antimicrobial or microbiocidal activity. In contrast, a preservative is generally described as an inhibitor or biostatic composition.

The Present Compositions

The present invention relates to peroxycarboxylic acid antimicrobial compositions, including ready-to-use compositions, which have advantageous sporicidal activity, advantageous stability, and/or advantageously reduced corrosiveness. In an embodiment, the present compositions unexpectedly have increased and more rapid activity against spores (e.g., bacterial or fungal spores) and/or viruses at room temperature. For example, embodiments of the present compositions have advantageous sporicidal activity against *Clostridium difficile* and difficult to kill bacterial endospores, such as those of *Clostridium sporogenes* and *Bacillus subtilis*. Further, the present compositions are also active against vegetative bacteria, vegetative fungi, other bacterial spores, fungal spores, and viruses. Labels of conventional sporicidal products state that they require 5 to 32 hours to kill spores at room temperature (i.e., ambient conditions). At least one embodiment of the present invention kills spores to the same level in only 30 minutes. This is surprisingly and advantageously only $\frac{1}{10}^{th}$ to $\frac{1}{64}^{th}$ of the time required by conventional products.

In an embodiment, the present compositions are unexpectedly less corrosive than conventional peroxycarboxylic acid compositions. Conventional corrosion inhibitors (e.g., triazole and fatty acid) are known to work at basic pH and the conventionally described mechanism of action requires basic pH. Applicants have unexpectedly discovered that, at acid pH, a mixture of medium chain mono carboxylic acid or benzoic acid derivative and corrosion inhibitor reduces corrosion compared to a composition lacking such a carboxylic acid and/or the corrosion inhibitor. In certain embodiments, the composition has pH of about 1 to about 5, about 1 to about 4.5, or about 1 to about 4 and includes medium chain mono carboxylic acid or benzoic acid derivative and corrosion inhibitor (e.g., triazole corrosion inhibitor). The present compositions can provide, at an acid pH, reduced corrosion of, for example, soft metals, such as mild steel, aluminum, or brass. In an embodiment the present composition corrodes brass at a rate of less than about 250 mil per year. In an embodiment the present composition corrodes brass at a rate of less than about 100 mil per year.

In an embodiment, the present compositions unexpectedly have increased storage stability, which allows the compositions to retain antimicrobial activity for longer times after they are made. Surprisingly, the present compositions retain high levels of peroxycarboxylic acid in the absence of significant levels of strong acid (e.g., sulfuric acid). In an embodiment, the present compositions do not include substantial strong acid. Although not limiting to the present invention, the storage stability of the present compositions is believed to result from the ratio of hydrogen peroxide to peroxycarboxylic acid and/or the ratio of hydrogen peroxide to protonated carboxylic acid. For example, the ratio of hydrogen peroxide to peroxycarboxylic acid can be about 30:1 to about 60:1. For example, the ratio of hydrogen peroxide to protonated carboxylic acid can be about 1:1 to about 2:1.

In certain embodiments, the composition includes a defined ratio of hydrogen peroxide to peroxycarboxylic acid, a defined ratio of hydrogen peroxide to protonated carboxylic acid, or a defined ratio of hydrogen peroxide to peroxycarboxylic acid and of hydrogen peroxide to protonated carboxylic acid. It is believed that the defined ratio is effective to provide prolonged shelf life to the compositions of the present invention. For example, the defined ratio or ratios can provide a composition of the invention that is storage stable for at least 1 month at 40° C., for 12 months at typical room temperatures (20-25° C.), or even longer at room temperature.

A storage stable composition, at the predetermined time limit, still contains an antimicrobially effective concentration of peroxycarboxylic acid. In certain embodiments, for example, at the predetermined time limit, a storage stable composition can have more than 75% of the initial concentration of peroxycarboxylic acid, more than 80% of the initial concentration of peroxycarboxylic acid, more than 85% of the initial concentration of peroxycarboxylic acid, more than 90% of the initial concentration of peroxycarboxylic acid, or more than 95% of the initial concentration of peroxycarboxylic acid. In an embodiment, at the predetermined time limit, a storage stable composition of the present invention has more than 85% of the initial concentration of peroxycarboxylic acid.

In certain embodiments, for example, at the predetermined time limit, a storage stable composition can have more than 80% of the initial concentration of medium chain carboxylic acid, more than 85% of the initial concentration of medium chain carboxylic acid, more than 90% of the initial concentration of medium chain carboxylic acid, or more than 95% of the initial concentration of medium chain peroxycarboxylic acid. In an embodiment, at the predetermined time limit, a storage stable composition of the present invention has more than 85% of the initial concentration of medium chain peroxycarboxylic acid.

In certain embodiments, for example, at the predetermined time limit, a storage stable composition can have more than 80% of the initial concentration of hydrogen peroxide, more than 85% of the initial concentration of hydrogen peroxide, more than 90% of the initial concentration of hydrogen peroxide, or more than 95% of the initial concentration of hydrogen peroxide. In an embodiment, at the predetermined time limit, a storage stable composition of the present invention has more than 85% of the initial concentration of hydrogen peroxide.

In an embodiment, at the predetermined time limit, the storage stable composition can have more than 80% of the initial concentration of peroxycarboxylic acid, more than 85% of the initial concentration of medium chain carboxylic acid, and more than 85% of the initial concentration of hydrogen peroxide. In an embodiment, at the predetermined time limit, the storage stable composition can have more than 85% of the initial concentration of peroxycarboxylic acid, more than 90% of the initial concentration of medium chain carboxylic acid, and more than 90% of the initial concentration of hydrogen peroxide.

In certain embodiments, the composition includes a defined ratio of hydrogen peroxide to peroxycarboxylic acid. In certain embodiments, the ratio of hydrogen peroxide to peroxycarboxylic acid is less than about 1000:1, about 5:1 to about 1000:1, about 13:1 to about 800:1, or about 16:1 to about 400:1. In certain embodiments, the ratio of hydrogen peroxide to peroxycarboxylic acid is about 10:1 to about 200:1, about 25:1 to about 100:1, about 30:1 to about 60:1, or about 50:1. These can be weight ratios or ratios of concentration, such as ppm. The composition can include any of these ratios or amounts not modified by about. In an embodiment, the compositions do not include a substantial amount of strong acid. In an embodiment, the compositions do not include a substantial amount of mineral acid.

In certain embodiments, the composition includes a defined ratio of hydrogen peroxide to protonated carboxylic acid. In certain embodiments, the ratio of hydrogen peroxide to protonated carboxylic acid is less than about 10:1, about 1:5 to about 10:1, about 0.5:1 to about 8:1, about 1:1 to about 8:1. In certain embodiments, the ratio of hydrogen peroxide to protonated carboxylic acid about 0.2:1 to about 10:1, about 0.5:1 to about 4:1, about 1:1 to about 2:1 or about 1.4:1. The composition can include any of these ratios or amounts not modified by about. These can be weight ratios or ratios of concentration, such as ppm. In an embodiment, the compositions do not include a substantial amount of strong acid. In an embodiment, the compositions do not include a substantial amount of mineral acid.

In certain embodiments, the composition includes a defined ratio of hydrogen peroxide to peroxycarboxylic acid and of hydrogen peroxide to protonated carboxylic acid. In certain embodiments, the ratio of hydrogen peroxide to peroxycarboxylic acid is about 10:1 to about 200:1 and the ratio of hydrogen peroxide to protonated carboxylic acid is about 0.2:1 to about 10:1, about 0.5:1 to about 4:1, about 1:1 to about 2:1, or about 1.4:1. In certain embodiments, the ratio of hydrogen peroxide to peroxycarboxylic acid is about 25:1 to about 100:1 and the ratio of hydrogen peroxide to protonated carboxylic acid is about 0.2:1 to about 10:1, about 0.5:1 to about 4:1, about 1:1 to about 2:1, or about 1.4:1. In certain embodiments, the ratio of hydrogen peroxide to peroxycarboxylic acid is about 30:1 to about 60:1 and the ratio of hydrogen peroxide to protonated carboxylic acid is about 0.2:1 to about 10:1, about 0.5:1 to about 4:1, about 1:1 to about 2:1, or about 1.4:1. In certain embodiments, the ratio of hydrogen peroxide to peroxycarboxylic acid is about 50:1 and the ratio of hydrogen peroxide to protonated carboxylic acid is about 0.2:1 to about 10:1, about 0.5:1 to about 4:1, about 1:1 to about 2:1, or about 1.4:1. The composition can include any of these ratios or amounts not modified by about. These can be weight ratios or ratios of concentration, such as ppm. In an embodiment, the compositions do not include a substantial amount of strong acid. In an embodiment, the compositions do not include a substantial amount of mineral acid.

In certain embodiments, the ratio of hydrogen peroxide to protonated carboxylic acid is about 0.2:1 to about 10:1 and the ratio of hydrogen peroxide to peroxycarboxylic acid is about 10:1 to about 200:1, about 25:1 to about 100:1, about 30:1 to about 60:1, or about 50:1. In certain embodiments, the ratio of hydrogen peroxide to protonated carboxylic acid is about 0.5:1 to about 4:1 and the ratio of hydrogen peroxide to peroxycarboxylic acid is about 10:1 to about 200:1, about 25:1 to about 100:1, about 30:1 to about 60:1, or about 50:1. In certain embodiments, the ratio of hydrogen peroxide to protonated carboxylic acid is about 1:1 to about 2:1 and the ratio of hydrogen peroxide to peroxycarboxylic acid is about 10:1 to about 200:1, about 25:1 to about 100:1, about 30:1 to about 60:1, or about 50:1. In certain embodiments, the ratio of hydrogen peroxide to protonated carboxylic acid is about 1.4:1 and the ratio of hydrogen peroxide to peroxycarboxylic acid is about 10:1 to about 200:1, about 25:1 to about 100:1, about 30:1 to about 60:1, or about 50:1. In certain embodiments, the ratio of hydrogen peroxide to protonated carboxylic acid is less than about 1.2:1 and the ratio of hydrogen peroxide to peroxycarboxylic acid is about 10:1 to about 200:1, about 25:1 to about 100:1, about 30:1 to about 60:1, or about 50:1. The composition can include any of these ratios or amounts not modified by about. These can be weight ratios or ratios of concentration, such as ppm. In an embodiment, the compositions do not include a substantial amount of strong acid. In an embodiment, the compositions do not include a substantial amount of mineral acid.

In an embodiment, the present compositions do not include substantial strong acid. Conventional peroxycarboxylic acid compositions include mineral acid to catalyze the formation of peroxycarboxylic acid from hydrogen peroxide and carboxylic acid. Surprisingly, the present inventors have made an effective antimicrobial peroxycarboxylic acid composition without substantial strong acid. That is, the present compositions do not include amounts of strong acid effective for catalyzing the reaction of hydrogen peroxide and carboxylic acid to form peroxycarboxylic acid.

In an embodiment, the present composition is free of strong acid, e.g., mineral acid. In an embodiment, the present composition is substantially free of strong acid, e.g., mineral acid. In an embodiment, the present composition is free of added strong acid, e.g., mineral acid. In certain embodiments, the present composition includes less than about 5 wt-% strong acid, less than about 4 wt-% strong acid, less than about 3 wt-% strong acid, less than about 2 wt-% strong acid, or less than about 1 wt-% strong acid. In an embodiment, the present composition includes less than about 1 wt-% strong acid. The composition can include any of these ranges or amounts not modified by about.

In certain embodiments, the present compositions advantageously have low eye corrosivity and/or advantageously masked odor. For example, a storage stable ready to use composition according to the present invention can have reduced toxicity compared to conventional concentrate compositions. For example, a storage stable ready to use composition according to the present invention can have its odor masked compared to a conventional concentrate composition that has been diluted with water.

Embodiments of the Present Compositions

Some examples of representative constituent concentrations for embodiments of the present compositions can be found in Tables A-C, in which the values are given in wt-% of the ingredients in reference to the total composition weight. In certain embodiments, the proportions and amounts in Tables A-C can be modified by "about".

TABLE A

| Ingredient | wt-% | wt-% | wt-% | wt-% | wt-% | wt-% |
|---|---|---|---|---|---|---|
| peroxycarboxylic acid | 0.005-0.2 | 0.015-0.15 | 0.03-0.1 | 0.02-0.12 | 0.04-0.08 | 0.06 |
| short chain carboxylic acid | 0.5-4 | 0.5-3.5 | 0.5-3 | 1-3 | 1.5-2.5 | 2 |
| medium chain or aromatic carboxylic acid | 0.01-0.3 | 0.01-0.25 | 0.01-0.2 | 0.04-0.2 | 0.07-0.15 | 0.1 |
| oxidizing agent | 1-5 | 2-4 | 2.5-4 | 2-4 | 2.5-3.5 | 3 |
| optionally, corrosion inhibitor | 0.01-0.25 | 0.01-0.2 | 0.01-0.15 | 0.01-0.2 | 0.04-0.08 | 0.06 |

TABLE B

| Ingredient | wt-% | wt-% | wt-% | wt-% | wt-% | wt-% |
|---|---|---|---|---|---|---|
| peroxycarboxylic acid | 0.005-0.2 | 0.015-0.15 | 0.03-0.1 | 0.02-0.12 | 0.04-0.08 | 0.06 |
| short chain carboxylic acid | 0.5-4 | 0.5-3.5 | 0.5-3 | 1-3 | 1.5-2.5 | 2 |
| medium chain or aromatic carboxylic acid | 0.01-0.3 | 0.01-0.25 | 0.01-0.2 | 0.04-0.2 | 0.07-0.15 | 0.1 |
| oxidizing agent | 1-5 | 2-4 | 2.5-4 | 2-4 | 2.5-3.5 | 3 |
| optionally, corrosion inhibitor | 0.01-0.25 | 0.01-0.2 | 0.01-0.15 | 0.01-0.2 | 0.04-0.08 | 0.06 |
| optionally, buffer | 0.01-2 | 0.01-1 | 0.01-0.8 | 0.1-0.3 | 0.15-0.25 | 0.2 |
| stabilizing agent | 0.01-3 | 0.01-2 | 0.01-1 | 0.04-0.2 | 0.07-0.15 | 0.1 |
| hydrotrope | 0.01-5 | 0.01-4 | 0.01-3 | 0.04-0.2 | 0.07-0.15 | 0.1 |
| surfactant | 0.01-5 | 0.01-4 | 0.01-3 | 0.1-1 | 0.3-0.5 | 0.4 |

TABLE C

| Ingredient | wt-% | wt-% | wt-% | wt-% | wt-% | wt-% |
|---|---|---|---|---|---|---|
| short chain peroxycarboxylic acid | 0.005-0.2 | 0.015-0.15 | 0.03-0.1 | 0.02-0.12 | 0.04-0.08 | 0.06 |
| medium chain peroxycarboxylic acid | 0.0001-0.004 | 0.0001-0.003 | 0.0001-0.002 | 0.0001-0.001 | 0.0001-0.0006 | 0.0001-0.0004 |
| short chain carboxylic acid | 0.5-4 | 0.5-3.5 | 0.5-3 | 1-3 | 1.5-2.5 | 2 |
| medium chain or aromatic carboxylic acid | 0.01-0.3 | 0.01-0.25 | 0.01-0.2 | 0.04-0.2 | 0.07-0.15 | 0.1 |
| oxidizing agent | 1-5 | 2-4 | 2.5-4 | 2-4 | 2.5-3.5 | 3 |
| optionally, corrosion inhibitor | 0.01-0.25 | 0.01-0.2 | 0.01-0.15 | 0.01-0.2 | 0.04-0.08 | 0.06 |
| optionally, buffer | 0.01-2 | 0.01-1 | 0.01-0.8 | 0.1-0.3 | 0.15-0.25 | 0.2 |
| stabilizing agent | 0.01-3 | 0.01-2 | 0.01-1 | 0.04-0.2 | 0.07-0.15 | 0.1 |
| hydrotrope | 0.01-5 | 0.01-4 | 0.01-3 | 0.04-0.2 | 0.07-0.15 | 0.1 |
| surfactant | 0.01-5 | 0.01-4 | 0.01-3 | 0.1-1 | 0.3-0.5 | 0.4 |
| masking agent | 0.01-1 | 0.01-0.8 | 0.01-0.6 | 0.04-0.2 | 0.07-0.15 | 0.1 |
| pH | 1-5 | 1.5-4.5 | 1.5-3.5 | 1-4 | 2.5-3.5 | 3 |

The compositions in these Tables can include carrier (e.g., water) to bring the total content up to 100 wt-%.

The compositions in Table C can have one or more advantageous qualities including: forming a dilute, stable, ready-to-use product; having enhanced biocidal activity against vegetative bacteria and fungi; having significantly enhanced sporicidal and virucidal activity; providing a good multi-surface detersive cleaner/one-step disinfectant; causing only low corrosion against soft metals, plastics and elastomers; being safe for the user (no mineral acid; low dermal, eye & nose irritation); and/or being environmentally friendly.

Unless stated otherwise, the concentrations of ingredients are when the composition is at equilibrium. Unless stated otherwise, the concentrations of ingredients refer to the active component and not to an amount of a commercial product that may include ingredients in addition to the active ingredient.

In an embodiment, the present antimicrobial composition includes about 2 wt-% to about 4 wt-% hydrogen peroxide, about 0.5 wt-% to about 3.5 wt-% acetic acid, about 0.01 wt-% to about 0.25 wt-% octanoic acid, about 0.005 wt-% to about 0.15 wt-% of peroxyacetic acid, and about 0.0001 wt-% to about 0.002 wt-% peroxyoctanoic acid. In an embodiment, the present antimicrobial composition includes about 2.5 wt-% to about 4 wt-% hydrogen peroxide, about 0.5 wt-% to about 3 wt-% acetic acid, about 0.01 wt-% to about 0.2 wt-% octanoic acid, about 0.005 wt-% to about 0.1 wt % of peroxyacetic acid, and about 0.0001 wt-% to about 0.002 wt-% peroxyoctanoic acid.

In an embodiment, the present antimicrobial composition includes about 1 wt-% to about 5 wt-% hydrogen peroxide, about 0.5 wt-% to about 4 wt-% acetic acid, about 0.01 wt-% to about 0.3 wt-% octanoic acid, about 0.005 wt-% to about 0.2 wt-% peroxyacetic acid, about 0.0001 wt-% to about 0.004 wt-% peroxyoctanoic acid, about 0.01 wt-% to about 2.5 wt-% sequestering agent, and about 0.01 wt-% to about 1.5 wt-% buffer.

In an embodiment, the present antimicrobial composition includes about 1 wt-% to about 5 wt-% hydrogen peroxide, about 0.5 wt-% to about 4 wt-% acetic acid, about 0.01 wt-% to about 0.3 wt-% octanoic acid, about 0.005 wt-% to about 0.2 wt-% peroxyacetic acid, about 0.0001 wt-% to about 0.004 wt-% peroxyoctanoic acid, about 0.01 wt-% to about 2.5 wt-% sequestering agent, about 0.01 wt-% to about 1.5 wt-% buffer, about 0.01 wt-% to about 5 wt-% hydrotrope.

In an embodiment, the present antimicrobial composition includes about 1 wt-% to about 5 wt-% hydrogen peroxide, about 0.5 wt-% to about 4 wt-% acetic acid, about 0.01 wt-% to about 0.3 wt-% octanoic acid, about 0.005 wt-% to about 0.2 wt-% peroxyacetic acid, about 0.0001 wt-% to about 0.004 wt-% peroxyoctanoic acid, about 0.01 wt-% to about 2.5 wt-% sequestering agent, about 0.01 wt-% to about 1.5 wt-% buffer, about 0.01 wt-% to about 5 wt-% hydrotrope and about 0.01 wt-% to about 5 wt-% surfactant.

In an embodiment, the present antimicrobial composition includes about 1 wt-% to about 5 wt-% hydrogen peroxide, about 0.5 wt-% to about 4 wt-% acetic acid, about 0.01 wt-% to about 0.3 wt-% octanoic acid, about 0.005 wt-% to about 0.2 wt-% peroxyacetic acid, about 0.0001 wt-% to about 0.004 wt-% peroxyoctanoic acid, about 0.01 wt-% to 2.5 wt-% sequestering agent, about 0.01 wt-% to about 1.5 wt-% buffer, about 0.01 wt-% to about 5 wt-% hydrotrope, about 0.01 wt-% to about 5 wt-% surfactant, about 0.01 wt-% to about 0.25 wt-% corrosion inhibitor, and about 0.01 wt-% to about 1 wt-% masking agent/fragrance.

In an embodiment, the present antimicrobial composition includes hydrogen peroxide, acetic acid, a $C_6$ to $C_{12}$ aliphatic carboxylic acid and reaction equilibrium quantities of a peroxyacetic acid and $C_6$ to $C_{12}$ peroxy carboxylic acid. In an embodiment, the present antimicrobial composition includes hydrogen peroxide, peroxyacetic acid, octanoic acid and peroxyoctanoic acid; a ratio of hydrogen peroxide to total peroxyacid of about 30:1 to about 60:1. In an embodiment, the present antimicrobial composition includes about 1 wt-% to about 5 wt-% hydrogen peroxide, about 0.5 wt-% to about 4 wt-% acetic acid, about 0.01 wt-% to about 0.3 wt-% octanoic acid, about 0.005 wt-% to about 0.2 wt-% of peroxyacetic acid, and about 0.0001 wt-% to about 0.004 wt-% peroxyoctanoic acid.

In an embodiment, the present antimicrobial composition includes a $C_6$ to $C_{12}$ aliphatic or an aromatic carboxylic acid and exhibits reduced corrosion of soft metals at a pH of about 3. Suitable carboxylic acids include hexanoic acid, heptanoic acid, octanoic acid, nonanoic acid, decanoic acid, undecanoic acid, dodecanoic acid, salicylic acid, or a mixture thereof. In an embodiment, the present antimicrobial composition includes surfactant, which delivers detersive effect upon microbe harboring soils and biofilms preventing such contaminants from shielding pathogens. In an embodiment, the present antimicrobial composition includes a stable odor masking fragrant component uniformly solubilized by aid of a surfactant. In an embodiment, the present antimicrobial composition also includes one or more surfactants, one or more sequestrant stabilizing agents, one or more hydrotropes, one or more fragrances, one or more corrosion inhibiting agents, one or more buffers, one or more additional adjuvants, water, or a mixture thereof.

The present compositions can be made by combining or mixing at least the ingredients required to form peroxycarboxylic acid and letting them react for a time sufficient to convert carboxylic acid to peroxycarboxylic acid. A sufficient reaction time can be, for example, from a few hours to 21 days.

In an embodiment, the compositions of the present invention include only ingredients that can be employed in food products or in food wash, handling, or processing, for example, according to government (e.g. FDA or USDA) rules and regulations, 21 CFR §170-178. In an embodiment, the compositions of the present invention can include only ingredients at the concentrations approved for incidental food contact by the USEPA, 40 CFR §180.940.

The present compositions can take the form of a liquid, gel, paste, unit dose, gel pack, unitized or compartmentalized tear or water soluble packet, or the like. The present compositions can be supplied in any of a variety of containers or media, such as in a hand held pump/spray container, a 2 compartment dispenser; or as a pre-moistened wipe, towelette, or sponge.

In an embodiment, the concentration of peroxyacetic acid is above 425 ppm for the lifetime of a product including an embodiment of a composition according to the present invention. In an embodiment, the concentration of octanoic acid is above 900 ppm for a product including an embodiment of a composition according to the present invention. In an embodiment, the concentration of hydrogen peroxide is above 2.85 wt-% for the lifetime of a product including an embodiment of a composition according to the present invention.

Compositions of Medium Chain Carboxylic Acids and/or Peroxycarboxylic Acids

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. The composition and methods of the invention can employ medium chain peroxycarboxylic acids containing, for example, 6 to 12 carbon atoms. For example, medium chain peroxycarboxylic (or percarboxylic) acids can have the formula $R(CO_3H)_n$, where R is a $C_5$-$C_{11}$ alkyl group, a $C_5$-$C_{11}$ cycloalkyl, a $C_5$-$C_{11}$ arylalkyl group, $C_5$-$C_{11}$ (e.g., $C_6$) aryl group, or a $C_5$-$C_{11}$ heterocyclic group; and n is one, two, or three.

Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide. In an embodiment, the medium chain percarboxylic acids can be made by the direct, acid catalyzed equilibrium action of hydrogen peroxide on the medium chain carboxylic acid. Scheme 1 illustrates an equilibrium between carboxylic acid and oxidizing agent (Ox) on one side and peroxycarboxylic acid and reduced oxidizing agent ($Ox_{red}$) on the other:

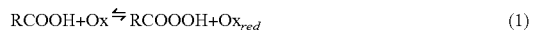

(1)

Scheme 2 illustrates an embodiment of the equilibrium of scheme 1 in which the oxidizing agent is hydrogen peroxide on one side and peroxycarboxylic acid and water on the other:

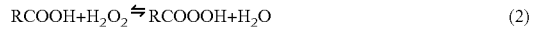

(2)

In conventional mixed peroxycarboxylic acid compositions it is believed that the equilibrium ratio for the reaction illustrated in scheme 2 is about 2.5, which may reflect the equilibrium for acetic acid.

Peroxycarboxylic acids useful in the compositions and methods of the present invention include peroxypentanoic, peroxyhexanoic, peroxyheptanoic, peroxyoctanoic, peroxynonanoic, peroxydecanoic, peroxyundecanoic, peroxydodecanoic, peroxysalicylic acid, peroxybenzoic acid, mixtures thereof, or the like. The alkyl backbones of the medium chain peroxycarboxylic acid can be straight chain, branched, or a mixture thereof. Peroxy forms of carboxylic acids with more than one carboxylate moiety can have one or more (e.g., at least one) of the carboxyl moieties present as peroxycarboxyl moieties.

Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of microbes.

The composition of the present invention can include a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention typically employ medium chain carboxylic acids containing, for example, 6 to 12 carbon atoms. For example, medium chain carboxylic acids can have the formula R—COOH in which R can be a $C_5$-$C_{11}$ alkyl group, a $C_5$-$C_{11}$ cycloalkyl group, a $C_5$-$C_{11}$ arylalkyl group, $C_5$-$C_{11}$ (e.g., $C_6$) aryl group, or a $C_5$-$C_{11}$ heterocyclic group.

Suitable medium chain carboxylic acids include pentanoic acid, hexanoic acid, heptanoic acid, octanoic acid, nonanoic acid, decanoic acid, undecanoic acid, dodecanoic acid, salicylic acid, benzoic acid, mixtures thereof, or the like. The alkyl backbones of the medium chain carboxylic acids can be straight chain, branched, or a mixture thereof. Carboxylic acids which are generally useful are those having one or two carboxyl groups where the R group is a primary alkyl chain having a length of $C_4$ to $C_{11}$. The primary alkyl chain is that carbon chain of the molecule having the greatest length of carbon atoms and directly appending carboxyl functional groups. Carboxylic acids which are generally useful are those having one carboxyl group as a substituent on a phenyl ring, such as salicylic acid or benzoic acid.

The present compositions and methods can include a medium chain peroxycarboxylic acid. The medium chain peroxycarboxylic acid can include or be a C6 to C12 peroxycarboxylic acid. The C6 to C12 peroxycarboxylic acid can include or be peroxyhexanoic acid, peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C7 to C12 peroxycarboxylic acid. The C7 to C12 peroxycarboxylic acid can include or be peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C6 to C10 peroxycarboxylic acid. The C6 to C10 peroxycarboxylic acid can include or be peroxyhexanoic acid, peroxyheptanoic acid, peroxyoctanoic acid, peroxynonanoic acid, peroxydecanoic acid, or mixture thereof. The medium chain peroxycarboxylic acid can include or be a C8 to C10 peroxycarboxylic acid. The C8 to C10 peroxycarboxylic acid can include or be peroxyoctanoic acid, peroxynonanoic acid, peroxydecanoic acid, or mixture thereof. In certain embodiments, the medium chain peroxyoctanoic acid includes or is peroxyoctanoic acid, peroxydecanoic acid, or mixture thereof. In an embodiment, the medium chain peroxycarboxylic acid includes or is peroxyoctanoic acid.

In certain embodiments, a composition of the invention can includes one or more peroxycarboxylic acids such as peroxyacetic acid, peroxyhexanoic acid, peroxyheptanoic acid, peroxyoctanoic acid, peroxynonanoic acid, peroxydecanoic acid, peroxyundecanoic acid, peroxydodecanoic acid, peroxysalicylic acid and peroxybenzoic acid. Such a peroxycarboxylic acid can be at a concentration of 0.001 to about 0.2 wt-%, about 0.005 wt-% to about 0.2 wt-%, about 0.005 wt-% to about 0.15 wt-%, or about 0.005 wt-% to about 0.1 wt-%. In an embodiment, the composition of the invention includes hydrogen peroxide and peroxycarboxylic acid at a ratio of hydrogen peroxide to total peroxycarboxylic acid about 10:1 to about 200:1, about 25:1 to about 100:1, about 30:1 to about 60:1, or about 50:1. This ratio can be based on weight percent or parts per million of total peroxycarboxylic acids present. The composition can include any of these ranges or amounts not modified by about. In an embodiment, the composition of the invention includes peroxyacetic acid and peroxyoctanoic acid.

In an embodiment, the present compositions and methods include a medium chain carboxylic acid. The medium chain carboxylic acid can include or be a C6 to C12 carboxylic acid. The C6 to C12 carboxylic acid can include or be hexanoic acid, heptanoic acid, octanoic acid, nonanoic acid, decanoic acid, undecanoic acid, dodecanoic acid, or mixture thereof. The medium chain carboxylic acid can include or be a C7 to C12 carboxylic acid. The C7 to C12 carboxylic acid can include or be heptanoic acid, octanoic acid, nonanoic acid, decanoic acid, undecanoic acid, dodecanoic acid, or mixture thereof. The medium chain carboxylic acid can include or be a C6 to C10 carboxylic acid. The C6 to C10 carboxylic acid can include or be hexanoic acid, heptanoic acid, octanoic acid, nonanoic acid, decanoic acid, or mixture thereof. The medium chain carboxylic acid can include or be a C8 to C10 carboxylic acid. The C8 to C10 carboxylic acid can include or be octanoic acid, nonanoic acid, decanoic acid, or mixture thereof. In certain embodiments, the medium chain carboxylic acid includes or is octanoic acid, decanoic acid, or mixture thereof. In an embodiment, the medium chain carboxylic acid includes or is octanoic acid. In an embodiment, the medium chain carboxylic acid includes or is salicylic acid.

The compositions can include an aliphatic medium chain mono carboxylic acid such as hexanoic acid, heptanoic acid, octanoic acid, or nonanoic acid; or a benzoic acid derivative. As used herein, the phrase "benzoic acid derivative" refers to benzoic acid and ring substituted benzoic acids (e.g., salicylic acid). These carboxylic acids effectively augment the reduction in corrosion in the presence of a corrosion inhibitor at acid pH, e.g., pH of about 1 to about 5, about 1 to about 4.5, or about 1 to about 4. The composition can include such a carboxylic acid and a corrosion inhibitor, such as a triazole corrosion inhibitor. The composition can include such a carboxylic acid at a concentration of about 0.01 to about 0.2 wt-%, about 0.01 to about 5 wt-%, about 0.5 wt-% to about 4 wt-%, about 0.5 wt-% to about 3 wt-%. The composition can include any of these ranges or amounts not modified by about.

In an embodiment, the compositions and methods include a medium chain peroxycarboxylic acid and the corresponding medium chain carboxylic acid.

In an embodiment, the present composition includes an amount of medium chain carboxylic acid effective for killing one or more (e.g., at least one) of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold, and the like. In an embodiment, the present composition includes an amount of medium chain carboxylic acid effective for killing one or more (e.g., at least one) of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, antibiotic resistant *Staphylococcus* (MRSA, VISA), community acquired antibiotic resistant *Staphylococcus* species, and the like. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Compositions of Short Chain Carboxylic Acids and/or Peroxycarboxylic Acids

The composition and methods of the invention can employ short chain peroxycarboxylic acids containing, for example, 1 to 4 carbon atoms. For example, short chain peroxycarboxylic (or percarboxylic) acids can have the formula $R(CO_3H)_n$, where R is H or a $C_1$-$C_3$ alkyl group and n is one, two, or three. In an embodiment, the short chain percarboxylic acids can be made by the direct, acid catalyzed equilibrium action of hydrogen peroxide on the short chain carboxylic acid. In conventional mixed peroxycarboxylic acid compositions it is believed that the equilibrium constant for the reaction illustrated in scheme 2 is about 2.5, which may reflect the equilibrium for acetic acid.

Peroxycarboxylic acids useful in the compositions and methods of the present invention include peroxyformic acid, peroxyacetic acid, peroxypropionic acid, and peroxybutyric acid, mixtures thereof, or the like. The alkyl backbones of certain of the propionic and butyric peroxycarboxylic acids can be straight chain, branched, or a mixture thereof. Peroxy forms of carboxylic acids with more than one carboxylate moiety can have one or more (e.g., at least one) of the carboxyl moieties present as peroxycarboxyl moieties. Peroxyacetic (or peracetic) acid is a peroxycarboxylic acid having the formula: $CH_3COOOH$. IN an embodiment, the short chain peroxycarboxylic acid includes or is peroxyacetic acid.

The composition of the present invention can include a short chain carboxylic acid. The composition and methods of the invention typically employ short chain carboxylic acids containing, for example, 2 to 4 carbon atoms. For example, short chain carboxylic acids can have the formula R—COOH in which R can be a H or a $C_1$-$C_3$ alkyl group. Suitable short chain carboxylic acids include formic acid, acetic acid, propionic acid, and butyric acid, mixtures thereof, or the like. The alkyl backbones propionic acid and butyric acid can be straight chain, branched, or a mixture thereof. In an embodiment, the short chain carboxylic acid is a hydroxycarboxylic acid (e.g., an α-hydroxycarboxylic acid), such as hydroxyacetic acid or hydroxypropionic acid. In an embodiment, the short chain carboxylic acid includes or is acetic acid. In an embodiment, the compositions and methods include a short chain peroxycarboxylic acid and the corresponding short chain carboxylic acid.

In an embodiment, the present composition includes an amount of short chain peroxycarboxylic acid effective for killing one or more (e.g., at least one) of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold, and the like. In an embodiment, the present composition includes an amount of short chain peroxycarboxylic acid effective for killing one or more (e.g., at least one) of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, antibiotic resistant *Staphylococcus* (MRSA, VISA), community acquired antibiotic resistant *Staphylococcus* species, and the like. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Oxidizing Agent

The present compositions and methods can include any of a variety of oxidizing agents. The oxidizing agent can be used for maintaining or generating peroxycarboxylic acids. Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water. For safety, the 35% is commonly used. The present compositions can include, for example, about 2 to about 30 wt-% or about 5 to about 20 wt-% hydrogen peroxide.

In an embodiment, the present compositions and methods can include hydrogen peroxide, urea peroxide, or cumene hydroperoxide as oxidizing agent. Hydrogen peroxide in combination with the percarboxylic acid can provide certain antimicrobial action against microorganisms. Additionally, hydrogen peroxide can provide an effervescent action which can irrigate any surface to which it is applied. Hydrogen peroxide can work with a mechanical flushing action once applied which further cleans the surface of an object. An additional advantage of hydrogen peroxide is the food compatibility of this composition upon use and decomposition. An oxidizing agent different from hydrogen peroxide can be employed at a concentration that provides equivalent oxidation or oxygen concentrations.

In certain embodiments, the composition of the present invention includes hydrogen peroxide (or another oxidizing agent) at about 0.3 to about 5% wt-%, about 1 wt-% to about 5 wt-%, about 2 wt-% to about 4 wt-%, or about 2.5 wt-% to about 4 wt-%. The composition can include any of these ranges or amounts not modified by about.

Carrier

The composition of the invention can also include a carrier. The carrier provides a medium which dissolves, suspends, or carries the other components of the composition. For example, the carrier can provide a medium for solubilization, suspension, or production of peroxycarboxylic acid and for forming an equilibrium mixture. The carrier can also function to deliver and wet the antimicrobial composition of the invention on an object. To this end, the carrier can contain any component or components that can facilitate these functions.

In certain embodiments, the carrier includes primarily water which can promote solubility and work as a medium for reaction and equilibrium. The carrier can include or be primarily an organic solvent. Polyols can be useful carriers, including glycerol, sorbitol, and the like.

Suitable carriers include glycol ethers. Glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

In certain embodiments, the carrier makes up a large portion of the composition of the invention and may be the balance of the composition apart from the active antimicrobial components, solubilizer, oxidizing agent, adjuvants, and the like. Here again, the carrier concentration and type will depend upon the nature of the composition as a whole, the environmental storage, and method of application including concentration of the peroxycarboxylic acid, among other factors. Notably the carrier should be chosen and used at a concentration which does not inhibit the antimicrobial efficacy of the peroxycarboxylic acid in the composition of the invention.

In certain embodiments, the present composition includes about 60 to about 99 wt-% carrier (e.g., water), about 70 to about 99 wt-% carrier (e.g., water), about 80 to about 97 wt-% carrier (e.g., water), about 85 to about 95 wt-% carrier (e.g., water), or about 90 to about 95 wt-% carrier (e.g., water). For example, in certain embodiments, the present composition can include about 70 wt-% carrier (e.g., water), about 75 wt-% carrier (e.g., water), about 80 wt-% carrier (e.g., water), about 85 wt-% carrier (e.g., water), about 90 wt-% carrier (e.g., water), or about 95 wt-% carrier (e.g., water).

Buffer

The present composition can include a buffer, such as a buffer effective to maintain the pH of the composition at an acid pH, e.g., about 1 to about 5, about 1 to about 4.5, or about 1 to about 4. Buffers suitable for such acid pHs are or include 3-(N-morpholino)propanesulfonic acid (MOPS), piperazine-N,N'-bis(2-ethanesulfonic acid) (PIPES), 2-(N-morpholino) ethanesulfonic acid (MES), N-(2-Acetamido)iminodiacetic Acid (ADA), sodium phosphate, sodium citrate, sodium formate, sodium malate, sodium acetate, or sodium diacetate. Suitable buffers are or include phosphate salt, citrate salt, formate salt, malate salt, or acetate salt. Suitable buffers are or include sodium phosphate, sodium citrate, sodium formate, sodium malate, or sodium acetate. A suitable buffer is or includes acetic acid and acetate (e.g., sodium acetate).

The present compositions can include the salt component of the buffer at, for example, about 0.01 to about 1.5 wt-%, about 0.05 to about 1 wt-%, or about 0.05 wt-% to about 0.8 (e.g., 0.75) wt-%. In certain embodiments, the present composition includes sodium acetate at about 0.01 to about 1.5 wt-%, about 0.05 to about 1 wt-%, or about 0.05 wt-% to about 0.8 (e.g., 0.75) wt-%.

Corrosion Inhibitor

The composition of the present invention can include a corrosion inhibitor. Suitable corrosion inhibitors include triazoles, such as benzotriazole (CAS no. 95-14-7) or tolytriazole (CAS no. 64665-57-2). A triazole corrosion inhibitor, such as benzotriazole, can be included at a concentration of about 0.01 to about 0.25 wt-%, about 0.01 to about 0.2 wt-%, or about 0.01 wt-% to about 0.15 wt-%.

Adjuvants

The antimicrobial composition of the invention can also include any number of adjuvants. Specifically, the composition of the invention can include stabilizing agent, antimicrobial agent, wetting agent, defoaming agent, thickener, a surfactant, foaming agent, a hydrotrope or coupling agent, a surfactant, aesthetic enhancing agent (i.e., colorant (e.g., pigment), odorant, perfume, fragrance, or masking agent), among any number of constituents which can be added to the composition. Such adjuvants can be preformulated with the antimicrobial composition of the invention or added to the system simultaneously, or even after, the addition of the antimicrobial composition. Additional suitable adjuvants include potentiators (also referred to as synergists to the active ingredients) rheology modifiers, manufacturing processing aids, preserving agents, or tracers. The composition of the invention can also contain any number of other constituents as necessitated by the application, which are known and which can facilitate the activity of the present invention.

An adjuvant can be selected to be compatible with the other components in the composition in the long term, for at least 6 months and preferably at least 12 months or longer at ambient room temperatures.

Stabilizing Agent

One or more stabilizing agents can be added to the composition of the invention, for example, to stabilize the peracid and hydrogen peroxide and prevent the premature degradation of this constituent within the composition of the invention.

Suitable stabilizing agents include chelating agents or sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or include phosphonic acid or phosphonate salt. Suitable phosphonic acids and phosphonate salts include 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetraethanolamine salts; or mixtures thereof.

Suitable organic phosphonates include HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

In certain embodiments, the present composition includes stabilizing agent at about 0.01 to about 3 (e.g., 2.5) wt-%, about 0.01 to about 2 (e.g., 2.5) wt-%, or about 0.01 to about 1.5 wt-%. The composition can include any of these ranges or amounts not modified by about.

Additional Antimicrobial Agent

The antimicrobial compositions of the invention can contain an additional antimicrobial agent. Additional antimicrobial agent can be added to use compositions before use. Suitable antimicrobial agents include sulfonic acids (e.g., dodecylbenzene sulfonic acid), phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride, N-dialkylethylbenzyl ammonium chloride, or mixtures thereof), and mixtures of such antimicrobial agents, in an amount sufficient to provide the desired degree of microbial protection.

The present composition can include an effective amount of antimicrobial agent, such as about 0.001 wt-% to about 10 wt-% antimicrobial agent, about 0.003 wt-% to about 5 wt-% antimicrobial agent, or about 0.01 wt-% to about 2.5 wt-% antimicrobial agent.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Suitable defoamers which can be used in accordance with the invention include aliphatic acids or esters; alcohols; sulfates or sulfonates; amines or amides; vegetable oils, waxes, mineral oils as well as their sulfated derivatives; fatty acid soaps such as alkali, alkaline earth metal soaps; and mixtures thereof.

In an embodiment, the present compositions can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetraalkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range of about 0.01 wt-% to 5 wt-%, about 0.01 wt-% to 2 wt-%, or about 0.01 wt-% to about 1 wt-%.

Thickening or Gelling Agents

The present compositions can include any of a variety of known thickeners. Suitable thickeners include inorganic thickeners, organic thickeners, oligomeric thickeners, and associative thickeners. These may include natural gums such as xanthan gum, guar gum, or other gums from plant mucilage; modified cellulose derivatives; oligomeric organic thickeners; and hydrocolloid thickeners, such as pectin and inorganic silicates and clays. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity of the final composition. However, as a general guideline, the quantity of thickener suitable for use in the present composition ranges about 0.1 wt-% to about 1.5 wt-%, about 0.1 wt-% to about 1 wt-%, or about 0.1 wt-% to about 0.5 wt-%.

Hydrotrope or Coupling Agent

A composition of the invention can also include a hydrotrope, also referred to as a coupling agent. A hydrotrope can increase the miscibility, solubility or phase stability of organic and inorganic materials in aqueous solution. A hydrotrope can also facilitate long term physical stability and/or homogenicity of a composition of the invention. A hydrotrope can be useful in a composition containing a carboxylic acid or peroxycarboxylic acid.

Suitable hydrotropes include nonaqueous liquid carriers or solvents. Suitable solvents include propylene oxide glycol ether (for example, a Dowanol® P Series (Dow Chemical, Midland, Mich.)) or an ethylene oxide based glycol ether. Suitable propylene oxide glycols include a dipropylene glycol n-propyl ether sold under the tradename Dowanol DPnB by Dow Chemical.

A stabilizing hydrotrope or coupling agent can be present in the composition at, for example, about 0.01 to about 5 wt-%, about 0.05 to about 4 wt-%, or about 0.05 to about 3 wt-%.

Surfactant

A composition of the invention may include a surfactant. Suitable surfactants include water-soluble or water dispersible nonionic, cationic, amphoteric, semipolar nonionic (e.g., zwitterionic) surface active agents.

The surfactant can be a nonionic surfactant. Suitable nonionic surfactant include a surfactant with ethylene oxide moieties, propylene oxide moieties or mixtures thereof, and surfactants with ethylene oxide-propylene oxide moieties in heteric, block or random heteric-block formation. Suitable nonionic surfactants include alkyl ethylene oxide surfactants, alkyl propylene oxide surfactants, alkyl ethylene oxide-propylene oxide surfactants, and alkyl ethylene oxide-propylene oxide surfactants in which the ethylene oxide-propylene oxide moiety is either in heteric, block or random hetericblock formation.

The nonionic surfactants can be a nonionic surfactant having any mixture or combination of ethylene oxide-propylene oxide moieties linked to an alkyl chain where the ethylene oxide and propylene oxide moieties may be in any randomized or ordered pattern and of any specific length. Nonionic moieties may be capped/terminated with a benzyl, alkoxy or short chain alkyl grouping.

The nonionic surfactants can be a condensation product of a saturated or unsaturated, straight or branched chain alcohol having from about 6 to 24 carbon atoms with about 3 to about 50 moles of ethylene oxide. The alcohol moiety can consist of mixtures of alcohols in the above delineated carbon range or it can consist of an alcohol having a specific number of carbon atoms within this range. Examples of commercial surfactants of this chemistry are available under the trade name of Surfonic® manufactured by Huntsman Corp., Austin, Tex. and Neodol® manufactured by Shell Chemical Co., Houston, Tex.

A surfactant or surfactant system employed in the composition of the present invention can be present at about 0.01 to about 5 wt-%, about 0.01 to about 4 wt-%, or about 0.01 to about 3 wt-%.

Fragrance or Masking Agent

In an embodiment, the present composition includes a fragrance or masking agent. The fragrance can be selected to avoid undesirable effects on the stability or efficacy of the composition. A masking agent is one or more fragrant ingredients that mask or conceal an irritating odor, such as that of acetic acid or peroxyacetic acid. In an embodiment, the masking agent is chemically stable in highly oxidative acidic systems for at least about 6 months at typical room temperatures (20-25° C.), or even at least about 12 months, 24 months, or longer. Suitable masking agents include Fragrance WS 22201 Clean Herbal Mod II®, manufactured by Wessels Fragrance, Englewood Cliffs, N.J.; Snappy Apple UP183078® and, Wintermint UP183077® manufactured by Givaudan Fragrance, Teaneck, N.J. The masking agent can be included at a concentration of about 0.01 to about 1 wt-%, about 0.01 to about 0.8 wt-%, or about 0.01 wt-% to about 0.5 wt-%.

Use Compositions

The present compositions include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the peroxycarboxylic acid compound. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

For example, a use composition can include about 0.01 to about 4 wt-% of a concentrate composition and about 96 to about 99.99 wt-% diluent; about 0.5 to about 4 wt-% of a concentrate composition and about 96 to about 99.5 wt-% diluent; about 0.5, about 1, about 1.5, about 2, about 2.5, about 3, about 3.5, or about 4 wt-% of a concentrate composition; about 0.01 to about 0.1 wt-% of a concentrate composition; or about 0.01, about 0.02, about 0.03, about 0.04, about 0.05, about 0.06, about 0.07, about 0.08, about 0.09, or about 0.1 wt-% of a concentrate composition. Amounts of an ingredient in a use composition can be calculated from the amounts listed above for concentrate compositions and these dilution factors.

Methods Employing the Present Peroxycarboxylic Acid Compositions

The present invention includes methods employing the peroxycarboxylic acid compositions. Typically, these methods employ the antimicrobial or bleaching activity of the peroxycarboxylic acid. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a stabilized ester peroxycarboxylic acid composition of the invention. Contacting can include any of numerous methods for applying a composition, such as spraying the composition, immersing the object in the composition, foam or gel treating the object with the composition, or a combination thereof.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compositions can be employed as a foaming or nonfoaming environmental sanitizer or disinfectant.

The antimicrobial compositions of the invention can be included in products such as sterilants, sanitizers, disinfectants, preservatives, deodorizers, antiseptics, fungicides, germicides, sporicides, virucides, detergents, bleaches, and hard surface cleaners.

The antimicrobial compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or as a boot or shoe sole dip for people.

The present compositions can be employed for reducing the population of pathogenic microorganisms, such as pathogens of humans, animals, and the like. The compositions can exhibit activity against pathogens including fungi, molds, bacteria, spores, and viruses, for example, *Trycophyton* sp., *Aspergillus* sp., *Staphylococcus* sp., antibiotic resistant *Staphylococcus* sp., *E. coli, Streptococcus* sp., *Enterococcus* sp., *Legionella* sp., *Pseudomonas* sp., *Mycobacterium* sp., *Clostridium* sp., influenza and hepatitis viruses, phages, and the like. Such pathogens can cause a variety of diseases and disorders, including tuberculosis, lung and tissue infections, septicemic infections, hemolytic gastroenteritis, influenza, hepatitis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions can be used on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

The present compositions can be employed for reducing the population of microbes, fruit flies, or other insect larva on a drain or other surface.

The composition may also be employed by dipping food processing equipment into the use solution, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compositions.

The present invention may be better understood with reference to the following examples. These examples are intended to be representative of specific embodiments of the invention, and are not intended as limiting the scope of the invention.

EXAMPLES

| Compositions According to the Present Invention wt-% | | | | | | |
|---|---|---|---|---|---|---|
| Ingredient | A | B | C | D | E | F |
| peroxyacetic acid | 0.14 | 0.12 | 0.065 | 0.060 | 0.055 | 0.035 |
| peroxyoctanoic acid | 0.07 | 0.07 | 0.05 | δ[4] | δ | δ |
| glacial acetic acid | 4 | 3 | 3 | 2 | 1.8 | 0.5 |
| octanoic acid | 0.2 | 0.2 | 0.15 | 0.15 | 0.1 | 0.1 |
| hydrogen peroxide | 5 | 5 | 3.5 | 3.2 | 3.2 | 1.8 |
| benzotriazole | 0.25 | 0.25 | 0.25 | 0.1 | 0.06 | 0.1 |
| sodium acetate | 1 | 0.75 | 0.5 | 0.25 | 0.15 | 0.1 |
| sequestrant[1] | 2 | 0.75 | 0.5 | 0.25 | 0.1 | 2.5 |
| hydrotrope[2] | 5 | 2.5 | 0.5 | 0.25 | 0.1 | 0.1 |
| nonionic surfactant[3] | 4 | 4 | 1.5 | 1.5 | 0.35 | 0.3 |
| fragrance | 0.3 | 0.3 | 0.2 | 0.1 | 0.1 | 0.1 |

[1]HEDP sold under the tradename DEQUEST ® 2010
[2]a dipropyleneglycol n-butyl ether sold under the tradename DOWANOL ® DPnB
[3]a mixture of nonionic surfactants sold under the tradenames SURFONIC ® L24-17 and SURFONIC ® 24-7
[4]δ Indicates that the amount of peroxyoctanoic acid was less than the limit of detection, 0.0004 wt-%. However, peroxyoctanoic acid is in equilibrium with octanoic acid and hydrogen peroxide and it should be present.

The balance of each of compositions A-F was water and each was at a pH of about 3.

Example 1

Storage Stability

This experiment demonstrates that embodiments of the present composition can have long shelf life, for example, a minimum shelf life of 1 year. For example, the antimicrobial components of the test composition E remain stable during accelerated storage stability experiments.

Materials and Methods

Hydrogen peroxide content was determined by an oxidation-reduction titration with potassium permanganate in an acidified water dilution of the sample. After the endpoint of this titration was reached, an excess of potassium iodide was added to the solution to measure concentration of peroxyacid. Potassium iodide reacted with peroxyacid to liberate iodine which was titrated with a standard solution of sodium thiosulfate.

Octanoic acid content is determined by reverse-phase high pressure liquid chromatography, refractive index detection and comparison of peak areas to an external standard. A Waters 4.6 mm/250 mm PN#WATO 54275 reverse-phase column was employed with an acetonitrile/acetic acid mobile phase.

Results

Table 1A shows the stability composition E when held for 5 weeks at 40° C. within a standard container. One month of stability at 40° C. is generally a good measure of stability for one year shelf life under typical conditions. It is desirable for the concentration of peroxyacetic acid to remain above 425 ppm after one month at 40° C. It is desirable for the concentration of octanoic acid to remain above 900 ppm after one month at 40° C. It is desirable for the concentration of hydrogen peroxide to remain above 2.85 wt-% after one month at 40° C.

TABLE 1A

40° C. Accelerated Storage Stability

|  | Time (Weeks) | Peroxyacetic Acid (ppm) | Octanoic Acid (wt-%) | $H_2O_2$ (wt-%) |
|---|---|---|---|---|
| Sample 1 | 0 | 600 | 0.095 | 3.2 |
|  | 2 | 530 | 0.094 | 3.2 |
|  | 4 | 560 | 0.097 | 3.2 |
|  | 5 | 580 | 0.096 | 3.2 |
| Sample 2 | 0 | 590 | 0.094 | 3.3 |
|  | 2 | 530 | 0.094 | 3.2 |
|  | 4 | 560 | 0.097 | 3.2 |
|  | 5 | 590 | 0.097 | 3.2 |
| Sample 3 | 0 | 580 | 0.094 | 3.2 |
|  | 2 | 520 | 0.094 | 3.2 |
|  | 4 | 570 | 0.095 | 3.2 |
|  | 5 | 580 | 0.096 | 3.2 |
| Sample 4 | 0 | 560 | 0.094 | 3.1 |
|  | 2 | 520 | 0.094 | 3.2 |
|  | 4 | 570 | 0.098 | 3.2 |
|  | 5 | 590 | 0.098 | 3.2 |
| Sample 5 | 0 | 560 | 0.092 | 3.2 |
|  | 2 | 520 | 0.095 | 3.3 |
|  | 4 | 580 | 0.097 | 3.2 |
|  | 5 | 610 | 0.096 | 3.3 |

Table 1B shows the stability of active antimicrobial components in composition RTU E of Table B when held for 13 months at ambient room temperatures (about 20° C. to about 25° C.) in a standard container. This testing confirms a minimum composition shelf life of biocidal efficacy and chemical stability of 1 year.

TABLE 1B

Long Term Ambient Temperature Storage Stability

|  | Time (Months) | Peroxyacetic Acid (ppm) | Octanoic Acid (wt-%) | $H_2O_2$ (wt-%) |
|---|---|---|---|---|
| Sample 1 | 0 | 600 | 0.095 | 3.2 |
|  | 5 | 560 | 0.096 | 3.3 |
|  | 6 | 530 | 0.103 | 3.3 |
|  | 9 | 540 | 0.092 | 3.3 |
|  | 12 | 530 | 0.104 | 3.2 |
|  | 13 | 530 | 0.093 | 3.3 |
| Sample 2 | 0 | 590 | 0.094 | 3.3 |
|  | 5 | 560 | 0.097 | 3.3 |
|  | 6 | 520 | 0.102 | 3.3 |
|  | 9 | 540 | 0.096 | 3.3 |
|  | 12 | 510 | 0.098 | 3.3 |
|  | 13 | 530 | 0.098 | 3.3 |
| Sample 3 | 0 | 580 | 0.094 | 3.2 |
|  | 5 | 560 | 0.097 | 3.2 |
|  | 6 | 530 | 0.101 | 3.4 |
|  | 9 | 560 | 0.096 | 3.3 |
|  | 12 | 530 | 0.098 | 3.3 |
|  | 13 | 540 | 0.097 | 3.3 |
| Sample 4 | 0 | 560 | 0.094 | 3.1 |
|  | 5 | 550 | 0.097 | 3.2 |
|  | 6 | 530 | 0.096 | 3.3 |
|  | 9 | 560 | 0.091 | 3.3 |
|  | 12 | 520 | 0.096 | 3.3 |
|  | 13 | 530 | 0.098 | 3.3 |
| Sample 5 | 0 | 560 | 0.092 | 3.2 |
|  | 5 | 550 | 0.098 | 3.3 |
|  | 6 | 540 | 0.098 | 3.3 |
|  | 9 | 560 | 0.090 | 3.3 |
|  | 12 | 530 | 0.097 | 3.3 |
|  | 13 | 540 | 0.093 | 3.2 |

Conclusion

Tables 1A and 1B show the activity of hydrogen peroxide, peroxyacetic acid and octanoic acid do not appreciably change in these stability studies. The stability of the RTU E antimicrobial components confirms a minimum biocidal efficacy and chemical stability of 1 year.

Example 2

Hospital Disinfection Efficacy

This experiment demonstrates that compositions of the present invention have antimicrobial activity that meets and exceeds the standards of efficacy for hospital disinfection.

Materials and Methods

Testing was conducted following the Association of Official Analytical Chemists (hereafter AOAC) Use-Dilution Method 955.14, 955.15 and 964.02, Official Methods of Analysis of the AOAC International, 15$^{th}$ edition, 2005. Testing was conducted at 425 ppm peroxyacetic acid. A composition was considered to have adequate antimicrobial activity when there was no growth in 59 of 60 tubes.

Composition E was tested. This composition was prepared to include 3.2 wt. % hydrogen peroxide, 1.8 wt-% glacial acetic acid, 1000 ppm octanoic acid, and about 500 ppm total peroxyacids.

Results

Table 2 shows antimicrobial activity of composition E that meets the standards of efficacy for hospital disinfection.

TABLE 2

Hospital Disinfection Antibacterial Efficacy

| Microbe | ATCC Accession No. | CFU/Tube (ave.) | Microbe Free Tubes |
|---|---|---|---|
| S. choleraesuis (4 minutes) | 6538 | $2.8 \times 10^6$ | 60/60 |
| S. aureus (4 minutes) | 10708 | $1.3 \times 10^7$ | 60/60 |
| P. aeruginosa (4 minutes) | 15442 | $2.5 \times 10^7$ | 60/60 |

Conclusion

Table 2 demonstrates that a composition of the present invention has antimicrobial activity that meets and exceeds the standards of efficacy for hospital disinfection. It disinfected sixty out of sixty tubes in a standard analysis for antimicrobial efficiency against hospital microbes.

Example 3

Disinfection Efficacy Against Additional Organisms

This experiment demonstrates that compositions of the present invention are effective against bacteria, such as those from healthcare and food preparation environments.

Materials and Methods

Testing was conducted as above but with only 10 stainless steel tube per organism. A composition was considered to have adequate antimicrobial activity when there was no growth in 10 of 10 tubes.

Results

Table 3 shows data for disinfection by composition E against additional organisms.

TABLE 3

Disinfection Efficacy Against Bacteria of Healthcare and Food Borne Illness

| Microbe | ATCC Accession No. | CFU/Tube (ave.) | Microbe Free Tubes |
|---|---|---|---|
| *Enterococcus facials* - VRE* (4 minutes) | 51299 | $2.3 \times 10^7$ | 10/10 |
| *Staphylococcus aureus* - MRSA* (4 minutes) | 33592 | $8.9 \times 10^5$ | 10/10 |
| *Escherichia coli* (4 minutes) | 11229 | $1.0 \times 10^7$ | 10/10 |
| *Escherichia coli* O157:H7 (4 minutes) | 43895 | $1.6 \times 10^7$ | 10/10 |
| *Klebsiella pneumoniae* (4 minutes) | 4352 | $5.4 \times 10^6$ | 10/10 |
| *Shigella flexneri* (4 minutes) | 9380 | $3.1 \times 10^7$ | 10/10 |
| *Proteus vulgaris* (4 minutes) | 13315 | $1.5 \times 10^7$ | 10/10 |
| *Enteroabacter aerogenes* (4 minutes) | 13048 | $1.6 \times 10^7$ | 10/10 |
| *Clostridium difficile* (vegetative) (4 minutes)) | 9689 | $2 \times 10^7$ | 10/10 |
| *Staphylococcus aureus* - VISA* (4 minutes) | HIP 5836 | $1.12 \times 10^6$ | 10/10 |

*Antibiotic resistant bacteria: VRE—Vancomycin Resistant *Enterococcus faecalis*; MRSA—Methicillin Resistant *Staphylococcus aureus*; VISA—Vancomycin-Intermediate/Resistant *Staphylococcus aureus*

Conclusion

The results in Table 3 demonstrate that a composition of the present invention was an effective disinfectant against numerous bacteria from healthcare and food borne illnesses. It disinfected ten out of ten tubes for all microbes tested above.

Example 4

Fungicidal Efficacy

This experiment demonstrates that compositions according to the present invention have antifungal activity against pathogenic fungus, yeast, and mildew.

Materials and Methods

Testing was conducted as in Example 2 with the following modifications. Stainless steel penicillin carriers were inoculated with a soil suspension at 1 mL per carrier and incubated. The soil suspension was aspirated off and the carriers were aseptically transferred to sterile petri dishes matted with filter paper. The petri dishes were covered and dried at 35° C. for 40 min. Following drying, the microorganism was aseptically transferred to individual tubes containing 10 mL of the test substance. After the 4 minute exposure period, the carriers were subsequently subcultured into individual tubes of the subculture medium.

Results

Table 4 shows data for fungicidal activity of composition E.

TABLE 4

Fungicidal Efficacy of the Present Compositions

| Microbe | ATCC Accession No. | CFU/Tube (ave.) | Microbe Free Tubes |
|---|---|---|---|
| Pathogenic Fungus | | | |
| *Trichophyton mentagrophytes* (Athletes' Foot) (4 minutes) | 9533 | $1.4 \times 10^7$ Conidia suspension | 60/60 |
| Yeast | | | |
| *Candida albicans* (5 minutes) | 10231 | $5.0 \times 10^6$ | 10/10 |
| Mildew | | | |
| *Aspergillus niger* (4 minutes) | 6275 | $8.8 \times 10^6$ Conidia suspension | 60/60 |

Conclusion

Table 4 demonstrates that a composition of the present invention was effective against common forms pathogenic fungus, yeast, and mildew. It resulted in complete kill, as represented by complete kill in 60 out of 60 tubes for each of pathogenic fungus, yeast, and mildew tested.

Example 5

Quantitative Tuberculocidal Efficacy

This experiment demonstrates that a composition according to the present invention has effective antimicrobial activity against *Mycobacterium bovis*—BCG, a tuberculodical microbe.

Materials and Methods

Testing follows standard U.S. EPA protocol for a quantitative tuberculocidal test. An embodiment of the composition of the present invention was diluted with sterile deionized water at 425 ppm and tested against *Mycobacterium bovis*—BCG. A composition was considered to have adequate antimicrobial activity when there was 5 $\log_{10}$ reduction in the population of mycobacteria.

Results

Table 5 shows results obtained from a 2.5 minute exposure of the mycobacterium to composition E.

TABLE 5

Quantitative Tuberculocidal Efficacy Test Results

| | | CFU/Plate 2.5 Minutes | | | | |
|---|---|---|---|---|---|---|
| Microbe | CFU/Tube (ave.) | $10^{-1}$ Dilution | $10^{-3}$ Dilution | CFU/Plate (ave.) | CFU/mL (ave.) | Log Reduction |
| *Mycobacterium bovis* | $6.8 \times 10^4$ | 0 0 | 0 0 | 0 | <2 | >5 |

TABLE 5-continued

Quantitative Tuberculocidal Efficacy Test Results

| Microbe | CFU/Tube (ave.) | CFU/Plate 2.5 Minutes | | CFU/Plate (ave.) | CFU/mL (ave.) | Log Reduction |
|---|---|---|---|---|---|---|
| | | $10^{-1}$ Dilution | $10^{-3}$ Dilution | | | |
| BCG 454C150 (2.5 minutes) | | 0 | 0 | | | |
| | | 0 | 0 | | | |
| | | 0 | 0 | 0 | <2 | >5 |
| | | 0 | 0 | | | |
| | | 0 | 0 | | | |
| | | 0 | 0 | | | |
| | | 0 | 0 | 0 | <2 | >5 |

Conclusion

A composition of the present invention was effective against tuberculocidals as measured by a standard U.S. EPA protocol. It demonstrated a greater than 5 log reduction of *mycobacterium bovis* in the assay. There were no surviving organisms, complete kill was achieved.

Example 6

Virucidal Efficacy

This experiment demonstrates that a composition of the present invention has effective virucidal activity against numerous common viruses.

Materials and Methods

Testing was conducted according to ASTM E1053-97. Briefly: The virus suspension was dried on an inanimate, nonporous surface. The antimicrobial was added over the dried virus as a use dilution solution or sprayed from an aerosol can or trigger spray container and exposed at the appropriate temperature for the recommended time. The virus titer of an untreated surface was determined by the median infective dose ($ID_{50}$) method of virus titration. Cytotoxicity to the host system of the antimicrobial at the tested concentration was determined by an $LD^{50}$ method. The virus-antimicrobial mixture was assayed in numerous units of the host system at a dilution just beyond the cytotoxicity range of the antimicrobial. The extent of virus inactivation by the antimicrobial was determined. Results are recorded as $\log_{10}$-virus inactivated.

Results

Table 6 shows virucidal activity of composition E diluted to 425 ppm peroxyacetic acid.

TABLE 6

Virucidal Efficacy Test Results

| Microbe | ATCC Accession No. | CFU/Tube (ave.) | CFU/Tube (ave.) - post | Log Reduction |
|---|---|---|---|---|
| Feline Calicivirus (Norwalk Surrogate) (4 minutes) | VR-782 | $10^{7.0}$ | $10^{1.5}$ | >5.47 log Complete Inactivation No Viable Virus |
| Human Coronavirus SARS (4 minutes) | VR-740 | $10^{4.5}$ | $<10^{0.5}$ | >4 log Complete Inactivation No Viable Virus |
| Human Immunodeficiency Virus (HIV) Type 1 (30 seconds) | Strain HTLV-III$_B$ | $10^{5.75}$ | $<10^{1.5}$ | >4 log Complete inactivation No Viable Virus |
| Respiratory Syncytial Virus (RSV) (4 minutes) | VR-26 | $10^{5.5}$ | $10^{1.5}$ | >4 log Complete Inactivation No Viable Virus |
| Avian Influenza A Serotype H5N3 (4 minutes) | VR-2072, Strain A | $10^{5.0}$ | $<10^{0.5}$ | >4.5 log Complete Inactivation No Viable Virus |
| Adenovirus Type 4 (4 minutes) | VR-4 | $10^{5.5}$ | $10^{1.5}$ | >4 log Complete Inactivation No Viable Virus |
| Rhinovirus Type 37 (4 minutes) | VR-1147, Strain 151-1 | $10^{5.25}$ | $<10^{0.5}$ | >4.75 log Complete Inactivation No Viable Virus |
| Rotavirus (4 minutes) | Strain WA | $10^{6.75}$ | $10^{1.5}$ | >5.25 log Complete Inactivation No viable Virus |
| Hepatitis B Virus | Duck Hepatitis B Virus | $10^{5.0}$ | $<10^{1.5}$ | >3.21 Complete Inactivation No Viable Virus |

Conclusion

Composition E showed effective anti viral activity against nine common viruses. There was no viable virus and complete inactivation after exposure to composition E for four minutes.

Example 7

A Composition of the Present Invention Kills Spores Fast at Room Temperature

This experiment demonstrates that a composition according to the present invention showed fast and effective sporicidal activity against spores of three spore forming pathogens when tested at room temperature.

Materials and Methods

Testing was conducted following AOAC Official Method 966.04, Sporicidal Activity of Disinfectants. Testing was conducted at using a composition according to the present invention at 425 ppm peroxyacetic acid. Sporicidal activity was measured at 20° C. A composition was considered to have adequate antimicrobial activity when there was no growth in 60 of 60 tubes.

Results

Table 7 shows results obtained for sporicidal activity of composition E.

TABLE 7

Sporicidal (Cold Sterilant Test) Efficacy Test Results

| Microbe | ATCC Accession No. | CFU/Tube (ave.) | Microbe Free Tubes |
|---|---|---|---|
| *Bacillus subtilis* - Porcelain Carriers (30 minutes) | 19659 | $3.0 \times 10^4$ | 60/60 |
| *Bacillus subtilis* - Sutures (30 minutes) | 19659 | $5.4 \times 10^4$ | 60/60 |
| *Clostridium sporogenes* - Porcelain Carriers (30 minutes) | 3584 | $5.3 \times 10^4$ | 60/60 |
| *Clostridium sporogenes* - Sutures (30 minutes) | 3584 | $1.8 \times 10^6$ | 60/60 |
| *Clostridium difficile* - Porcelain Carriers (20 minutes) | 9689 | $6.8 \times 10^4$ | 60/60 |
| *Clostridium difficile* - Sutures (20 minutes) | 9689 | $1.1 \times 10^4$ | 60/60 |

TABLE 8

Comparison of Sporicidal Activity With Commercial Products

| Composition (Active Ingredient(s)) | Time Required for Effective Sporicidal Action[1] |
|---|---|
| Inventive Composition E (3.15% hydrogen peroxide, 424 ppm peroxyacetic acid, 950 ppm octanoic acid) | 30 minutes at 25° C. |
| Commercial Product A (5.75% ortho-phthaldehyde (OPA)) | 32 hours at 50° C.[2] |
| Commercial Product B (1.12% Glutaraldehyde and 1.93% phenol/phenate) | 12 hours at 25° C. |
| Commercial Product C (hypochlorite and hypochlorous acid, 650-675 ppm active free chlorine) | 24 hours at 25° C. |
| Commercial Product D (8.3% Hydrogen Peroxide and 7.0% Peroxyacetic Acid) | 5 hours at 25° C. |
| Commercial Product E (7.5% Hydrogen Peroxide) | 6 hours at 20° C. |

[1]Results reported for commercial products are provided by each manufacturer for testing in AOAC Sporicidal Activity Test or a modified version of that test. Center for Devices and Radiological Health, Office of Device Evaluation, U.S. Food and Drug Administration, http://www.fda.gov/cdrh/ode/germlab.html
[2]Tested as use solution containing 0.05% OPA Conclusion Composition E demonstrated effective sporicidal activity against six common microbes. Sixty out of sixty tubes were microbe free after no more than thirty minutes incubation with composition E. Composition E kills spores in $\frac{1}{10}^{th}$ to $\frac{1}{64}^{th}$ the amount of time of several commercial products.

Example 8

A Composition of the Present Invention Kills *B. cereus* Spores in a Test for Aseptic Packaging of Foods This experiment demonstrates that a composition according to the present invention showed fast and effective sporicidal activity against spores of *B. cereus* when tested for suitability in aseptic packaging for foods.

Materials and Methods

Sporicidal activity was measured against spores of *Bacillus cereus* ATCC with a 19 second exposure time at 60° C. using composition E at 490 ppm peroxyacetic acid. A composition was considered to have adequate antimicrobial activity when there was no growth in 30 of 30 tubes.

Results

In each of two tests, composition E killed the *B. cereus* spores in 30 of 30 stainless steel tubes.

Conclusion

Composition E demonstrated effective sporicidal activity against *B. cereus* spores. Thirty out of thirty tubes were microbe free after no more than 19 sec exposure to composition E.

Example 9

A Composition of the Present Invention is of Low Toxicity

This example demonstrates that a composition of the present invention showed no or little adverse reaction in standard texts of toxicity.

Materials and Methods

Toxicity testing was performed according to EPA Health Effects Test Guidelines, OPPTS 870.1000, Acute Toxicity Testing, December 2002. Testing was performed with composition E at a concentration of 3.2%-3.3 wt-% hydrogen peroxide, 450-550 ppm peroxyacetic acid, 950-1000 ppm octanoic acid, and <4 ppm peroxyoctanoic acid.

Results

In a test of toxicity from acute inhalation, composition E had an $LC_{50}$ of >2.31 mg/L. Composition E had an $LD_{50}$ of >5000 mg/kg in a test of toxicity from acute oral administration. In a test of toxicity from acute dermal contact, composition E had an $LD_{50}$ of >5000 mg/kg. This composition tested as only a slight irritant in a test for primary skin irritation. Each of these tests place it in category IV, the lowest level of toxicity, in the EPA standards. The composition is not a contact sensitizer in a test of dermal sensitization. The composition caused some eye irritation.

Example 10

Low Corrosion by the Present Compositions

This experiment demonstrates that a composition of the present invention showed a low corrosion rate as measured on brass CDA 360.

inhibitor provides a greater decrease in corrosion than would be expected by comparison to compositions including only the carboxylic acid or only the triazole corrosion inhibitor. Compositions K, N, and P corroded brass to only less than 100 mil/year (i.e., 57 mil, 69 mil, and 87 mil, respectively). Interestingly, compositions including mandelic acid, adipic acid, and a mixture of adipic, glutaric and succinic acids did not exhibit reduced corrosion. The compositions were at pH 3.

Compositions G-N were determined to be stable when held for one month at 40° C. within a typical commercial-type container according to the standards described above in Example 1.

TABLE 9

Brass CDA 360 Corrosion Results

| | wt-% | | | | | | | | | | | |
|---|---|---|---|---|---|---|---|---|---|---|---|---|
| | G | H | I | J | K | L | M | N | O | P | Q | R |
| Glacial Acetic Acid | 1.75 | 1.75 | 1.75 | 1.74 | 1.75 | 1.75 | 1.75 | 1.75 | 1.76 | 1.76 | 1.76 | 1.76 |
| Sequestrant | 0.10 | 0.10 | 0.12 | 0.12 | 0.10 | 0.10 | 0.10 | 0.10 | 0.10 | 0.10 | 0.10 | 0.10 |
| Hydrogen Peroxide, 35% | 9.00 | 9.00 | 8.98 | 8.98 | 9.00 | 9.00 | 9.00 | 9.01 | 9.08 | 9.08 | 9.08 | 9.07 |
| Nonionic surfactant | 0.30 | 0.30 | 0.30 | 0.30 | 0.30 | 0.30 | 0.43 | 0.43 | 0.30 | 0.30 | 0.30 | 0.30 |
| Nonionic surfactant | 0.05 | 0.05 | 0.05 | 0.05 | 0.05 | 0.05 | 0.05 | 0.06 | 0.05 | 0.05 | 0.05 | 0.06 |
| Sodium Acetate | 0.14 | 0.13 | 0.15 | 0.15 | 0.13 | 0.14 | 0.14 | 0.13 | 0.16 | 0.13 | 0.13 | 0.13 |
| Solvent | 0.10 | 0.10 | 0.10 | 0.10 | 0.10 | 0.10 | 0.10 | 0.10 | 0.11 | 0.10 | 0.10 | 0.10 |
| Fragrance | 0.10 | 0.10 | 0.10 | 0.10 | 0.10 | 0.10 | 0.10 | 0.10 | 0.10 | 0.11 | 0.11 | 0.11 |
| Hexanoic Acid | 0.10 | 0.10 | — | — | — | — | — | — | — | — | — | — |
| Heptanoic Acid | — | — | 0.10 | 0.10 | — | — | — | — | — | — | — | — |
| Octanoic Acid | — | — | — | — | 0.10 | 0.10 | — | — | — | — | — | — |
| Nonanoic Acid | — | — | — | — | — | — | 0.10 | 0.10 | — | — | — | — |
| Mandelic Acid | — | — | — | — | — | — | — | — | 0.10 | — | — | — |
| Salicylic Acid | — | — | — | — | — | — | — | — | — | 0.10 | — | — |
| Adipic Acid | — | — | — | — | — | — | — | — | — | — | 0.10 | — |
| Adipic, Glutaric, and Succinic Acids* | — | — | — | — | — | — | — | — | — | — | — | 0.10 |
| Benzotriazole | — | 0.06 | — | 0.07 | 0.06 | — | — | 0.06 | 0.06 | 0.06 | 0.06 | 0.06 |
| Deionized Water | 88.36 | 88.31 | 88.35 | 88.29 | 88.31 | 88.36 | 88.23 | 88.15 | 88.17 | 88.20 | 88.20 | 88.20 |
| Trial 1 Corrosion (mpy)** | 689 | 100 | 673 | 53 | 57 | 780 | 784 | 69 | 753 | 87 | 705 | 684 |
| Trial 2 Corrosion (mpy) | 693 | 112 | 685 | 55 | — | 786 | 790 | 70 | | | | |

*mixture of these acids sold under the tradename Sokolan DCS
**mpy - mils per year (mil = 0.001 inch)

Materials and Methods

Corrosion testing was performed according to ASTM G1-90 and G31-72. Compositions of the invention were tested for corrosion of coupons of brass CDA 360. The testing included weighting a clean, dry metal coupon, immersing the coupon in the test composition for 8 hours at 50° C. The coupons are then removed, dried, and weighed again. The weight loss is converted to thickness loss based on the surface area and density of the coupon. The measurements are compared to a water control. Compositions tested include peroxycarboxylic acid compositions and with and without hexanoic acid and/or benzotriazole or heptanoic acid and/or benzotriazole.

Results

Table 9 and FIG. 1 show results obtained for testing corrosion of brass by composition E and control compositions. The results show that a composition containing a medium chain carboxylic acid (e.g., hexanoic acid, heptanoic acid, octanoic acid, or nonanoic acid) and a triazole corrosion Conclusion Compositions according to the present invention and including a medium chain mono carboxylic acid (e.g., hexanoic acid, heptanoic acid, octanoic acid, and nonanoic acid) or a benzoic acid derivative (e.g., benzoic acid and salicylic acid) and a triazole corrosion inhibitor caused a significantly lower corrosion rate as measured on brass CDA 360 when compared to compositions including only the carboxylic acid or the corrosion inhibitor.

Example 11

Cleaning Performance

This experiment demonstrates that a composition of the present invention was an effective detergent as measured by the ability to remove soil. Bacteria, fungi or viruses held within the soil are treated more effectively when an antimicrobial component is mixed with a detergent component.

Materials and Methods

Three different soils were used for testing. A fatty food soil including fat, oil, and an iron compound was representative of residual food soils typically found on kitchen, food process, food preparation, food serving environmental surfaces and the like. A black oily soil largely including petroleum distillate, oil, and earth was representative of water insoluble greasy/oily soils, such as those carried onto surfaces from the general environment, cosmetics, equipment, instruments, tools, devices and the like. An inorganic bathtub/shower soil including minerals, soapy residue, and synthetic dead skin cells represented inorganic hard water deposits and soap scum found on typical bathroom and sink area surfaces. Tests using the fatty food soil and black food soil were generally performed according to ASTM D 4488-95. Tests using the Inorganic Bathtub/Shower Soil were generally performed according to ASTM D 5343-97.

Results

Table 10 shows the cleaning results obtained for composition E of the present invention against the fatty food soil, the black oily soil, and the inorganic bathtub/shower soil. Cleaning performance against each soil was measured by wt-% removal of the soil from the surface being cleaned.

TABLE 10

Soil Cleaning Performance Results Summary

| Soil | Soil Removal (wt-%) |
|---|---|
| Fatty Food Soil | 87 |
| Black Oily Soil | 51 |
| Inorganic Bathtub/Shower Soil | 62 |

Conclusion

Composition E of the present invention demonstrated effective detergent action against three common types of soil that an antimicrobial composition would be used on. The detergent removed and suspended soil so that the antimicrobial component can destroy the bacteria, fungi or viruses held within the soil and upon the surface being treated.

Example 12

Glass Cleaning Performance

This experiment demonstrated that a composition of the present invention was an effective glass cleaner.

Procedure

Composition E was tested for glass cleaning performance according to CSMA Detergents Division Test Method Designation DCC-09 ($3^{rd}$ ed., 1995) with the following test soil modification: 1% beef suet in hexane. Soil application, cleaning and rating follow the DCC-09 protocol. Results were graded by visual ranking on a scale of 1 to 4 for cleaning (soil removal), streaking, and smearing. A rating of 4 is best and a rating of 1 is poorest result.

Results

Table 11 shows that composition E scores consistently better than four common commercial products in all three categories tested.

TABLE 11

Glass Cleaning Performance Results

| | Cleaning | | Streaking | | Smearing | |
|---|---|---|---|---|---|---|
| Composition | Average Rating 1-4 | Standard Deviation | Average Rating 1-4 | Standard Deviation | Average Rating 1-4 | Standard Deviation |
| Commercial Product 1 | 1.8 | 0.4 | 1.0 | 0.0 | 2.6 | 0.7 |
| Commercial Product 2 | 2.3 | 0.5 | 2.0 | 0.9 | 2.8 | 0.4 |
| Commercial Product 3 | 1.9 | 0.5 | 1.4 | 0.5 | 2.5 | 0.5 |
| Commercial Product 4 | 2.2 | 0.8 | 1.8 | 1.0 | 2.3 | 0.8 |
| Composition E | 3.2 | 0.3 | 2.8 | 0.3 | 2.9 | 0.1 |

Cleaning, Streaking, and Smearing Rating Protocol**

| Cleaning: | Streaking: | Smearing: |
|---|---|---|
| 4 = Total soil removal | 4 = None | 4 = None |
| 3 = Good soil removal | 3 = Slight streaking | 3 = Slight smear |
| 2 = Moderate soil removal | 2 = Moderate streaking | 2 = Moderate smear |
| 1 = Poor soil removal | 1 = Severe streaking | 1 = Severe smear |

*All products were prediluted and ready-to-use
**Average of 2 tests, 3 individual graders Conclusion Composition E showed better glass cleaning performance than the four common commercial products it was tested against. It had an average higher score and a lower standard deviation for all three categories within the glass cleaning test.

Example 13

Additional Compositions According to the Present Invention

Additional compositions according to the present invention were assessed for their stability in an accelerated test and were demonstrated to be stable for the equivalent of 1 year at ambient conditions.

Materials and Methods

Stability was measured generally as described as in Example 1 for the compositions listed on Table 12 below.

TABLE 12

Additional Compositions According to the Present Invention wt-%

| Ingredient | E-1 | S | T | U | V | W | X | Y |
|---|---|---|---|---|---|---|---|---|
| glacial acetic acid | 1.7 | 1.8 | 1.8 | 1.8 | 1.8 | 1.5 | 1.7 | 1.8 |
| octanoic acid | 0.11 | 0.10 | — | 0.10 | 0.11 | 0.10 | 0.11 | 0.10 |
| hydrogen peroxide (35%) | 9.0 | 9.0 | 9.0 | 9.0 | 7.7 | 9.0 | 9.0 | 9.0 |
| benzotriazole | 0.06 | 0.08 | — | 0.06 | 0.06 | 0.05 | 0.06 | 0.06 |
| sodium acetate | 0.19 | 0.16 | 0.16 | 0.14 | 0.14 | 0.19 | 0.16 | 0.17 |
| sequestrant[1] | 0.09 | 0.11 | 0.11 | — | 0.11 | 0.11 | 0.13 | 0.13 |
| hydrotrope[2] | 0.11 | 0.10 | 0.10 | 0.10 | 0.11 | 0.12 | 0.10 | 0.10 |
| first nonionic surfactant[3] | 0.32 | — | — | 0.38 | 0.32 | 0.31 | — | — |
| second nonionic surfactant[4] | 0.05 | 0.04 | 0.05 | 0.05 | 0.06 | 0.06 | 0.05 | 0.05 |
| third nonionic surfactant[5] | — | — | — | — | — | — | 0.21 | — |
| lauryl amine oxide (30%) | — | — | — | — | — | — | — | 1.00 |
| fragrance | 0.10 | 0.10 | — | 0.11 | 0.09 | 0.10 | 0.10 | 0.10 |
| pH | 3.3 | 3.1 | 3.0 | 3.3 | 3.0 | 3.2 | 3.1 | 3.3 |

[1]HEDP sold under the tradename DEQUEST® 2010, percent listed is the commercial product which is 60% HEDP.
[2]a dipropyleneglycol n-butyl ether sold under the tradename DOWANOL® DPnB.
[3]linear alcohol (c12-c14) 17 mole ethoxylate sold under the tradename SURFONIC® L24-17.
[4]linear alcohol c12-c14 7 mole ethoxylate sold under the tradename SURFONIC® 24-7.
[5]eo/po block copolymer with avg m.w. 14,600 sold under the tradename PLURONIC F108.

The balance of each of compositions E-1 and S—Y was water. The amounts of ingredients are the amounts of raw materials added before the peroxycarboxylic acid was formed.

Results

Results of the stability testing of compositions E-1 and S—X are listed Table 13 below.

TABLE 13

Stability of Compositions E-1 and S-Y

| Days Since Formulation | Composition/ppm peroxycarboxylic acid | | | | | | | |
|---|---|---|---|---|---|---|---|---|
|  | E-1 | S | T | U | V | W | X | Y |
| 0 | 495 | 659 | 718 | 161 | 631 | 499 | 697 | 121 |
| 33 | 459 | 480 | 540 | 261 | 438 | 446 | 526 |  |

In each composition, the amount of peroxycarboxylic acid at 33 days was greater than or equal to 425 ppm. These compositions are stable compositions according to the present invention.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A shelf stable peroxycarboxylic acid composition comprising:
    (a) about 0.005 wt-% to about 0.2 wt-% of a $C_1$-$C_4$ short chain peroxycarboxylic acid;
    (b) about 1 wt-% to about 5 wt-% hydrogen peroxide;
    (c) about 0.01 wt-% to about 0.3 wt-% of a protonated $C_6$-$C_{12}$ medium chain carboxylic acid;
    (d) about 0.5 wt-% to about 3.5 wt-% of a protonated $C_1$-$C_4$ short chain carboxylic acid;
    (e) about 0.01 wt-% to about 2 wt-% buffer;
    (f) about 70 wt-% to about 99 wt-% water;
    (g) about 0.01 wt-% to about 5 wt-% nonionic surfactant;
    (h) about 0.01 to about 3 wt-% sequestrant comprising a phosphonic acid, phosphonate salt, or combinations of the same; and
    (i) about 0.01 wt-% to about 0.25 wt-% triazole corrosion inhibitor;
    wherein:
    the composition is free of added mineral acid;
    the pH of the composition is about 1 to about 4;
    the ratio of hydrogen peroxide:peroxycarboxylic acid in the composition is about 30:1 to about 60:1;
    the ratio of hydrogen peroxide:protonated carboxylic acid in the composition is about 1:1 to about 2:1; and
    wherein the composition is stable such that greater than 85% of the initial concentration of peroxycarboxylic acid remains after 1 year of storage at room temperature.

2. The composition of claim 1, comprising: about 0.015 wt-% to about 0.15 wt-% $C_1$-$C_4$ short chain peroxycarboxylic acid; and about 1 wt-% to about 3 wt-% protonated $C_1$-$C_4$ short chain carboxylic acid.

3. The composition of claim 1, comprising: about 0.01 wt-% to about 0.25 wt-% protonated $C_6$-$C_{12}$ medium chain carboxylic acid.

4. The composition of claim 1, further comprising a hydrotrope.

5. The composition of claim 1, the buffer comprising phosphate salt, citrate salt, formate salt, malate salt, or acetate salt.

6. The composition of claim 1, the buffer being an acetate salt.

7. The composition of claim 1, comprising about 0.01 wt-% to about 0.2 wt-% of the triazole corrosion inhibitor.

8. The composition of claim 1, comprising about 0.04 wt-% to about 0.08 wt-% of the triazole corrosion inhibitor.

9. The composition of claim 8, wherein the corrosion inhibitor comprises benzotriazole.

10. The composition of claim 1, further comprising about 0.01 to about 1 wt-% masking agent, the masking agent being chemically stable the composition for at least about 6 months at room temperature.

11. A low corrosion peroxycarboxylic acid composition comprising:
    (a) about 0.015 wt-% to about 0.15 wt-% of a $C_1$-$C_4$ short chain peroxycarboxylic acid;
    (b) about 2 wt-% to about 4 wt-% hydrogen peroxide;
    (c) about 0.01 wt-% to about 0.3 wt-% of a protonated $C_6$-$C_{12}$ medium chain carboxylic acid;
    (d) about 0.5 wt-% to about 3.5 wt-% of a protonated $C_1$-$C_4$ short chain carboxylic acid;
    (e) about 0.01 wt-% to about 2 wt-% buffer;
    (f) about 70 wt-% to about 99 wt-% water;
    (g) about 0.01 wt-% to about 0.25 wt-% corrosion inhibitor comprising a trazole;
    (h) about 0.01 wt-% to about 4 wt-% nonionic surfactant;

(i) about 0.01 to about 3 wt-% sequestrant comprising a phosphonic acid, phosphonate salt, or combinations of the same;

wherein:

the ratio of hydrogen peroxide:peroxycarboxylic acid in the composition is about 30:1 to about 60:1; and the ratio of hydrogen peroxide:protonated carboxylic acid in the composition is about 1:1 to about 2:1;

the composition is free of added mineral acid;

the pH of the composition is about 1 to about 4; and wherein the composition is stable such that greater than 85% of the initial concentration of peroxycarboxylic acid remains after 1 year of storage at room temperature.

12. The composition of claim 11, comprising about 0.01 wt-% to about 0.2 wt-% of the corrosion inhibitor.

13. The composition of claim 11, wherein the corrosion inhibitor comprises benzotriazole.

14. The composition of claim 11, wherein the buffer comprises a phosphate salt, citrate salt, formate salt, malate salt, or acetate salt.

15. The composition of claim 11, wherein the buffer being an acetate salt.

16. The composition of claim 11, comprising: about 0.02 wt-% to about 0.12 wt-% $C_1$-$C_4$ short chain peroxycarboxylic acid; and about 1 wt-% to about 3 wt-% protonated $C_1$-$C_4$ short chain carboxylic acid.

17. The composition of claim 11, comprising: about 0.01 wt-% to about 0.25 wt-% protonated $C_6$-$C_{12}$ medium chain carboxylic acid.

18. The composition of claim 11, further comprising a hydrotrope.

19. The composition of claim 11, wherein the composition causes less than 200 mil per year corrosion of brass.

20. The composition of claim 11, further comprising about 0.01 to about 1 wt-% masking agent, the masking agent being chemically stable the composition for at least about 6 months at room temperature.

21. A method of reducing the population of bacterial endospores, comprising:

contacting bacterial endospores with a composition comprising:

(a) about 0.0005 wt-% to about 0.2 wt-% of a $C_1$-$C_4$ short chain peroxycarboxylic acid;

(b) about 1 wt-% to about 5 wt-% hydrogen peroxide;

(c) about 70 wt-% to about 99 wt-% water;

(d) about 0.01 wt-% to about 0.3 wt-% of a protonated $C_6$-$C_{12}$ medium chain carboxylic acid;

(e) about 0.5 wt-% to about 3.5 wt-% of a protonated $C_1$-$C_4$ short chain carboxylic acid;

(f) about 0.01 wt-% to about 2 wt-% buffer;

(f) about 0.01 wt-% to about 5 wt-% nonionic surfactant;

(h) about 0.01 to about 3 wt-% sequestrant comprising a phosphonic acid, phosphonate salt, or combinations of the same; and (i) about 0.01 wt-% to about 0.25 wt-% benzotriazole corrosion inhibitor;

wherein: the composition is free of added mineral acid;

the pH of the composition is about 1 to about 4;

the ratio of hydrogen peroxide:peroxycarboxylic acid in the composition is about 30:1 to about 60:1;

the composition is stable such that greater than 85% of the initial concentration of peroxycarboxylic acid remains after 1 year of storage at room temperature; and the ratio of hydrogen peroxide:protonated carboxylic acid in the composition is about 1:1 to about 2:1; and achieving greater than 5 log reduction in the population of bacterial endospores in less than 1 hour under ambient conditions.

* * * * *